(12) United States Patent
Allen et al.

(10) Patent No.: US 7,605,247 B1
(45) Date of Patent: Oct. 20, 2009

(54) NUCLEIC ACID MOLECULES ENCODING A WHEAT SUCROSE TRANSPORTER

(75) Inventors: Stephen M. Allen, Wilmington, DE (US); William D. Hitz, Wilmington, DE (US); J. Antoni Rafalski, Wilmington, DE (US)

(73) Assignee: E.I. du Point de Nemours and Company, Wilmington, DE (US)

( * ) Notice: Subject to any disclaimer, the term of this patent is extended or adjusted under 35 U.S.C. 154(b) by 0 days.

(21) Appl. No.: 11/901,765

(22) Filed: Sep. 18, 2007

Related U.S. Application Data

(60) Division of application No. 09/679,687, filed on Oct. 5, 2000, now Pat. No. 7,288,645, which is a continuation of application No. PCT/US1999/007562, filed on Apr. 7, 1999.

(60) Provisional application No. 60/081,148, filed on Apr. 9, 1998.

(51) Int. Cl.
| | |
|---|---|
| *C12N 15/29* | (2006.01) |
| *C12N 15/82* | (2006.01) |
| *C12N 5/04* | (2006.01) |
| *C12N 5/10* | (2006.01) |
| *C12N 5/00* | (2006.01) |
| *A01H 5/00* | (2006.01) |

(52) U.S. Cl. ............... 536/23.6; 435/252.3; 435/320.1; 435/412; 435/415; 435/419; 435/424; 435/426; 435/469; 435/470; 800/278; 800/290; 800/312; 800/320.1; 800/320.2; 800/320.3

(58) Field of Classification Search .................. None
See application file for complete search history.

(56) References Cited

U.S. PATENT DOCUMENTS

| 5,750,362 A | 5/1998 | Frommer et al. |
|---|---|---|
| 6,025,544 A | 2/2000 | Leggewie et al. |
| 2003/0221224 A1 | 11/2003 | Zinselmeier et al. |

OTHER PUBLICATIONS

Aoki et al (2002. Plant Molecular Biology. 50: 453-462).*
Aoki et al (2006. Plant Physiol. 141(4): 1255-1263).*
J. W. Riesmeier et al., "Isolation and characterization of a sucrose carrier cDNA from spinach . . . ," The EMBO Journal, vol. 11, No. 13, pp. 4705-4713, 1992.
D.R. Bush, "Proton-coupled sugar and amino acid transporters in plants," Annu. Rev. Plant Physiol. Plant Mol. Biol., vol. 44, pp. 513-542, 1993.
L. Bisson et al., "Yeast Sugar Transporters" Crit. Rev. Biochem. Mol. Biol., 28(4): 259-308, 1993.
J. W. Riesmeier et al., "Evidence for an essential role of the sucrose transporter in phloem loading and assimilate . . . ," The EMBO Journal, vol. 13, No. 1, pp. 1-7 1994.
C. Kunh et al., "Companion Cell-Specific Inhibition Of The Potato . . . ", Plant, Cell And Environment (1996) 19, pp. 1115-1123.
R. Lemoine et al., "Antisense Inhibition Of the Sucrose Transporter . . . ", Plant, Cell and Environment (1996) 19, pp. 1124-1131.
T. Hirose, 1997, Accession No. BAA24071.
T. Hirose, National Center For Biotechnology Information General Identifier No. 2723471, Dec. 26, 1997.
T. Hirose et al., "cDNA Cloning and Tissue Specific Expression of a Gene for Sucrose Transporter from Rice (*Oryza sativa* L)", Plant Cell Phys., vol. 38(12): 1389-1396, 1997.
H. Weber, et al,. "A role for sugar transporters during seed development . . . ", National Center For Biotechnology Information, General Identifier No. 1935019, Apr. 9, 1997.
J.M. Ward et al., "Sucrose Transport in Higher Plants," International Review of Cytology, vol. 178, pp. 41-71, 1998.
L. Burkle et al., "The H+- Sucrose Cotransporter NtSUT1 Is Essential for Sugar Export from Tobacco Leaves," Plant Physiol., vol. 118 pp. 59-68, 1998.
R. Shakya et al., "Characterization of source -and sink-specific sucrose/H+ symporters from Carrot" Plant Physiol., vol. 118:1473-1480, 1998.
R. Shakya et al., "Characterization of source- and sink specific sucrose/H+ symporters" National Center For Biotechnology Information General Identifier No. 2969887, Jan. 13, 1999.
A.Sturm, 1999, Accession No. CAA76367.
Noiraud, et al., 1999 Accession No. GI4091891.
Aoki et al., "Molecular Cloning and Expression Analysis of a Gene for a Sucrose Transporter in Maize (*Zea mays* L.)," Plant Cell Physiol., 40 (10), pp. 1072-1078, 1999.
E. P. Wilhelm et al., "Crop Physiology & Metabolism," Crop. Sci. 39: 1733-1741, 1999.
A. Weig et al., National Center for Biotechnology Information General Identifier No. 542020, May 26, 2000.
R. Lemoine, "Sucrose transporters in plants: update on function and structure", Biochimica et Biophysica Acta 1465 pp. 246-262, 2000.
E. Truernit, 2001. "Plant physiology: The Importance of surcrose transpoerters." Current Biology. 11:R169-R171.
Federal Register, 2001, vol. 66, No. 4, pp. 1092-1099.
Ken Ishimau et al., "Antisense Expression of a Rice Sucrose Transporter OsSUT1 in Rice (*Oryza sativa* L.)," Plant Cell Physiol., vol. 42, 10, pp. 1181-1185, 2001.
C. F. Hainey et al. "Maize Mapping Project/DuPont Consensus Sequence . . . ," NCBI Accession No. AY106212, *Zea mays* PC0103031 mRNA sequence, Oct. 16, 2002.
G.N. Scofield et al., "Antisense suppression of the rice sucrose transporter gene, OsSUT1, leads to impaired grain filling . . . ," Funct. Plant Biol., vol. 29, pp. 815-826, 2002.

(Continued)

*Primary Examiner*—Bridget E Bunner
*Assistant Examiner*—Zachary C Howard

(57) ABSTRACT

This invention relates to an isolated nucleic acid fragment encoding a sucrose transport protein. The invention also relates to the construction of a chimeric gene encoding all or a portion of the sucrose transport protein, in sense or antisense orientation, wherein expression of the chimeric gene results in production of altered levels of the sucrose transport protein in a transformed host cell.

6 Claims, 6 Drawing Sheets

OTHER PUBLICATIONS

Christina Kuhn, "The Sucrose Transporter StSUT1 Localizes To Sieve . . . ", Plant Physiology, vol. 131, pp. 102-113, Jan. 2003.

A. L. Aoki et al., "The Sucrose Trasporter Gene Faily in Rice," Plant Cell Physiol, 44(3):223-232, 2003.

National Center for Biotechnology Information, General Identifier No. 54873545, Accession No. AY780256.1, Nov. 3, 2004.

A. L. Rae et al., "Sucrose partitioning between vascular bundles and storage parenchyma in the sugarcane stem: . . . " Planta, vol. 220, pp. 817-825, 2005.

EMBL Database Sequence Accession No. X75382, Oct. 7, 1993, N. K. Sauer et al., A thaliana SUC2 mRNA for sucrose-porton symporter.

EMBL Database Sequence Accession No. D40522, Nov. 11, 1994, T. Sasaki et al., Rice cDNA from callus 1995.

EMBL Database Sequence Accession No. D40515, Nov. 11, 1994, T. Sasaki et al., Rice cDNA from callus 1995.

Swissprot Database Sequence Accession No. Q03411, Jun. 1, 1994, J. W. Riesmeier et al., Isolation and characterization of a Sucrose cDNA from spinach.

EMBL Database Sequence Accession No. Q40937, Nov. 1, 1996, M. Gahrtz et al., SUC1-Sucrose Proton Symporter.

EMBL Database Sequence Accession No. Q43653, Nov. 1, 1996, J. Riesmeier et al., Sucrose trasnport protein from *Solanum tuberosum*.

EMBL Database Sequence Accession No. Q39232, Nov. 1, 1996, N. K. Sauer et al., Sucrose-proton trasporter protein SUC1 from *Arbidopsis thaliana*.

EMBL Database Accession No. Q41152, Nov. 1, 1996, A. Weig et al., Sucrose carrier from *Ricinus communis*.

EMBL Database Sequence Accession No. Z93774, Apr. 9, 1997, H. Weber et al., V faba mRNA for sucrose transporter.

EMBL Database Sequence Accession No. O04077, Jul. 1, 1997, H. Weber et al., Sucrose transport protein.

EMBL Database Sequence Accession No. AC000132, Feb. 28, 1997, V. S. Vysotkaia et al., Sequence of BAC F21M12 from *Arabidopsis thaliana* chromosome 1.

EMBL Database Sequence Accession No. O04516, Jun. 1, 1997, V.S. Vysotskaia et al., Similar to Vicica Sucrose Trasport protein.

EMBL Database Accession No. Z93774, Apr. 9, 1997, H. Weber et al. V faba mRNA for sucrose transporter.

EMBL Database Sequence Accession No. D87819, Jan. 5, 1998, T. Hirose "*Oryza sativa* mRNA for sucrose trasnporter."

* cited by examiner

FIGURE 1A

```
                               1                                                           60
SEQ ID NO:25 (gi 2969887)  MAG-------------------------------------PEADRNRHRGGATAAPPP-----
SEQ ID NO:26 (gi 2723471)  MARGSGAGGGGGGG----------------GGGLEL--------SVGVGGGG-ARGGGGEAAAAVET
SEQ ID NO:27 (gi 542020)   MQS-------------------------------------STSKENKQPPSSQPHPPPLMVAGAAE
SEQ ID NO:28 (gi 1935019)  MEP-------------------------------------LSSTKQINNNNLAKPSSLHVETQP-
SEQ ID NO:2                MARG-----------DG--------GQLAEL---------SAGVRG---------AAAVVDH
SEQ ID NO:4                HE--------------------------------------------------------------
SEQ ID NO:6                AA--------------------------------------------------------DH
SEQ ID NO:8                ----------------------------------------------------------------
SEQ ID NO:10               MDSAAGGGGLTAIRLPYRHLR-DAEMELVSLN------GGTPRGGSPKDPDATHQ-QGPPA
SEQ ID NO:12               ME--------------------------------------------------------EPQ
SEQ ID NO:14               MEP-------------------------------LSSTKH----NNNLSKPSSLHTEAPP-
SEQ ID NO:16               AR--------------------------------------------------------------
SEQ ID NO:18               ----------------------------------------------------------------
SEQ ID NO:20               MARG-----------GG----------NGEVEL-------SVGVGGGG---GAAGGEQPAVD-
SEQ ID NO:22               MARG-----------GG----------NGEVEL-------SVGVGGGA--GA-GGADAPAVD-
SEQ ID NO:24               --------------------------------------GSDAARPKEEQGSGAGAGEGG 61                                                         120
SEQ ID NO:25 (gi 2969887)  RSRVSLRLLLRVASVACGIQFGWALQLSLLTPVQELGIPHAWSSIIWLCGPLSGLLVQP
SEQ ID NO:26 (gi 2723471)  AAPISLGRLILSGMVAGGVQYGWALQLSLLTPVVQTLGLSHALTSFMWLCGPIAGMVVQP
SEQ ID NO:27 (gi 542020)   PNSSPLRKVVMVASIAAGIQFGWALQLSLLTPVVQLLGIPHTWAAFIWLCGPISGMLVQP
SEQ ID NO:28 (gi 1935019)  LEPSPLRKIMVVASIAAGVQFGWALQLSLLTPVVQLLGIHHTWAAYIWLCGPISGMLVQP
SEQ ID NO:2                VAPISLGRLILAGMVAGGVQYGWALQLSLLTPVVQTLGLSHALTSFMWLCGPIAGLVVQP
SEQ ID NO:4                ----------------------------------------------------------------
SEQ ID NO:6                ------------------------------------HEIT----------------------
SEQ ID NO:8                ----------------------------------------------------------------
SEQ ID NO:10               ARTTTTRKLVLACMVAAGVQFGWALQLSLLTPYIQTLGIDHAMASFIWLCGPITGFVVQP
SEQ ID NO:12               PGPSPLRKMILVSSMAAGIQFGWALQLSLLTPVVQTLGVPHAWASFIWLCGPISGLLVQP
SEQ ID NO:14               PEASPLRKIMVVASIAAGVQFGWALQLSLLTPVVQLLGIPHTWAAFIWLCGPISGMLVQP
SEQ ID NO:16               ---GW-----------------------------------------------------------
SEQ ID NO:18               ----------------------------------------------------------------
SEQ ID NO:20               ---ISLGRLILAGMVAGGVQYGWALQLSLLTPVVQTLGLSHALTSFMWLCGPIAGLVVQP
SEQ ID NO:22               ---ISLGRLILAGMVAGGVQYGWALQLSLLTPVVQTLGLSHALTSFMWLCGPIAGLVVQP
SEQ ID NO:24               MKGAPKWRVLACMVAAGVQFGWALQLSLLTPYIQTLGIDHAMASFIWLCGPITGFVVQP
```

FIGURE 1B

```
                              121                                                                         180
SEQ ID NO:25 (gi 2969887)    IVGHMSDQCTSKYGRRRPFIVAGGTAIILAVIIAHSADIGGLLGDT---AD----NKTM
SEQ ID NO:26 (gi 2723471)    CVGLYSDRCTSKWGRRRPYILTGCVLICLAVVIGFSADIGYAMGDTKEDCSVYHGSRWH
SEQ ID NO:27 (gi 542020)     IVGYHSDRCTSRFGRRRPFIASGAAFVAIAVFLIGYAADLGHLSGDSLDK-S----PKTR
SEQ ID NO:28 (gi 1935019)    IVGYHSDRCTSRFGRRRPFIAAGSIAVAIAVFLIGYAADLGHSFGDSLDQ-K----VRPR
SEQ ID NO:2                  LVGLYSDRCTSRWGRRRPFILTGCMLICVAVIVGFSSDIGAALGDTKEHCSLYHGPRWH
SEQ ID NO:4                  ------------------------------------------------------------
SEQ ID NO:6                  LVGLYSDRCTARWGRRRPFILIGCMLICLAVIVVGFSSDIGAALGDTKEHCSLYHGPRWH
SEQ ID NO:8                  ------------------------------------ASIAAAVLTVGFSADLGRIFGDSITPGS----TRLG
SEQ ID NO:10                 CVGVWSDKCRSKYGRRRPFILAGCLMICFAVTLIGFSADLGYILGDTTEHCST*YKGSRFR
SEQ ID NO:12                 IVGYSSDRCQSRFGRRRPFILAGSLAVAIAVFLIGYAADIGHAAGDNLTQ-K----TRPR
SEQ ID NO:14                 IVGYHSDRCTSRFGRRRPFIAAGSLAVAIAVFLIGYAADLGHMFGDSLAK-K----TAPR
SEQ ID NO:16                 ------------------------------------------------------------
SEQ ID NO:18                 ------------------------------------------------------------
SEQ ID NO:20                 CVGLYSDKCTSRWGRRRPFILTGCILICIAVVVGFSADIGAGLGDSKEECSLYHGPRWH
SEQ ID NO:22                 CVGLYSDKCTSRWGRRRPFILTGCILICIAVVVGFSADIGAALGDSKEECSLYHGPRWH
SEQ ID NO:24                 CVGVWSDKCRSKYGRRRPFILAGCVLICAAVTLVGFSADLGYMLGDTTEHCSTYKGLRYR 181                                                                         240
SEQ ID NO:25 (gi 2969887)    AIVAFVIGFWILDVANNMTQGPCRALLADLTGNDARRTRVANAYFSLFMAIGNVLGYATG
SEQ ID NO:26 (gi 2723471)    AAIVYVLGFWLLDFSNNTVQGPARALMADLSGRHGPGT--ANSIFCSWMAMGNILGYSSG
SEQ ID NO:27 (gi 542020)     AIIYLVGFWILDVGNNATQGPCRAFLADLTENDPRRTRIANAYFSLFMALGNILGYATG
SEQ ID NO:28 (gi 1935019)    AIAIFVVGFWMLDLANNTVQGPARALLADLSGPDQCNS--ANAIFCTWMAVGNVLGFSSG
SEQ ID NO:2                  AIGIFVVGFWILDVANNMLQGPCRAFLGDLAAGDEKKTKAANAFFSFFMAVGNVLGYAAG
SEQ ID NO:4                  HR-IFVVGFWILDVANNMLQGPCRALLGDLCAGEQRKTRNANAFFSFFMAVGNVLGYAAG
SEQ ID NO:6                  AAIVYVLGFWILDFSNNTVQGPARAMMADICDHHGPSA--ANSIFCSWMALGNILGYSSG
SEQ ID NO:8                  ------------------------------------------------------------
SEQ ID NO:10                 AAIVYVLGFWILDFSNNTVQGPARAMMADICGHHGPSA--ANSIFCSWMALGNILGYSSG
SEQ ID NO:12                 AIIYLVGFWILDVGNNATQGPCRAFLADLTENDPRRTRIANAYFSLFMALGNILGYATG
SEQ ID NO:14                 AAIFVLGFWMLDLANNTVQGPARALLADLSGPDQCNS--ANAIFCTWMAVGNVLGFSSG
SEQ ID NO:16                 AVAIFVIGFWILDVANNMLQGPCRAFLGDLAAGDEKKTKAANAFFSFFMAVGNVLGYAAG
SEQ ID NO:18                 HR-IFVVGFWILDVANNMLQGPCRALLGDLCAGEQRKTRNANAFFSFFMAVGNVLGYAAG
SEQ ID NO:20                 AAIVYVLGFWILDFSNNTVQGPARALMADLSAQHGPSA--ANSIFCSWMALGNILGYSSG
SEQ ID NO:22                 AAIVYVLGFWILDFSNNTVQGPARALMADLSAQHGPSA--ANSIFCSWMALGNILGYSSG
SEQ ID NO:24                 AAFIFIFGFWMLDLANNTVQGPARALLADLSGPDQCNS--ANAIFCSWMAVGNVLGFSAG
```

FIGURE 1C

```
                         241                                                                            300
SEQ ID NO:25 (gi 2969887) AYSGWYKVFPFSLTSSCTINCANLKSAFYIDIIFIIITTYISISAAKERPRISSQDGP-----
SEQ ID NO:26 (gi 2723471) STNNWHKWFPFLKTRACCEACANLKGAFLVAVIFLSLCLVITLIFAKEVPFKGNAA-------
SEQ ID NO:27 (gi 542020)  AYTHLYKLFPFTKTTACDVYCANLKSCFFISIVLLLSLTVLALSYVKEKPWSPDQAVD-----
SEQ ID NO:28 (gi 1935019) AYSKLYHVFPFTKACNVYCANLKSCFFLSIALLTVLATSALIYVKETALTPEKTVV-------
SEQ ID NO:2               STNNWHKWFPFLKTSACCEACANLKGAFLVAVVFLVLCLTVLIFAKEVPYRANEN-------
SEQ ID NO:4
SEQ ID NO:6               STNNWHKWFPFLMTNACCEACANLKGAFLVAVVFLIMCLTITLFFAKEVPYRGNQN-------
SEQ ID NO:8               AYSGWYKIFPFTVTPSCSISCANFKSAFLLDIIILVVTTCITVASV-------QEPQ------
SEQ ID NO:10              ASGNWHKWFPFLMTRACCEACSNLKAAFLVAVFLLFCMSVTLYFAEEIPLEPTDAQRLS
SEQ ID NO:12              SYDGLHRLFPFTETEACNVFCANLKSCFFFAIVLLVVLTTLVLITVKETPYTPKAEKE-----
SEQ ID NO:14              SYSGLHNVFPFTKTKACDVYCANLKSCFFLSIALLTLSTIALTYVKEKTVSSEKTVR-----
SEQ ID NO:16
SEQ ID NO:18
SEQ ID NO:20              STNNWHKWFPFLRTRACCEACANLKGAFLVAVLVLAFCLVITVIFAKEIPYKAIAP------
SEQ ID NO:22              STNNWHKWFPFLRTRACCEACANLKGAFLVAVLVLFLAFCLVITVIFAKEIPYKAIAP-----
SEQ ID NO:24              ASGNWHKWFPFLMTRACCEACGNLKAAFLIAVVFLLFCMAVTLYFAEEIPLEPKDAQQLS 301                                                                            360
SEQ ID NO:25 (gi 2969887) -----------------------------QFSEDGTAQSGHIEEA----F------
SEQ ID NO:26 (gi 2723471) -----------------------------------------------------G
SEQ ID NO:27 (gi 542020)  ------------------------NAEDDTASQASSAQPMFF---------
SEQ ID NO:28 (gi 1935019) ------------------------TT-EDGGSSGG-----MPCF-------
SEQ ID NO:2               -----------------------------------------------------G
SEQ ID NO:4               ----LPT-KSNEPAEPEGT-------------------------------
SEQ ID NO:6               ----LPTTKAGGEVETEPT-------------------------------
SEQ ID NO:8               ----LPT-KANGEVETEPS-------------------------------G
SEQ ID NO:10              DSAPLNGSRDDNNASNEPRNGALPNGHTDG---SNVPANSNAE-DSNSNRENVEVFNDG
SEQ ID NO:12              -------------------------------SFGSDEADHPSTEQEA---F------
SEQ ID NO:14              ------------------------------TEDAEKT------HFSCF-------
SEQ ID NO:16              ------------------------------SSVEEDGSHGG-----MPCF-------
SEQ ID NO:18              -----------------------------------------------------G
SEQ ID NO:20              ----LPT-KGNGQVEVEPT-------------------------------G
SEQ ID NO:22              ----LPT-KANGQVEVEPT-------------------------------G
SEQ ID NO:24              DSAPLNGSRDDHDASSEQTNGGLSNGHADA---NHVSANSSADAGSNSNKDDVEAFNDG
```

FIGURE 1D

```
                              361                                                               420
SEQ ID NO:25 (gi 2969887)     ----LWELFGTFRLLPGSVWILLVTCLNWIGWFPFILFDTDWMGREIYGGEPNQ---GQ
SEQ ID NO:26 (gi 2723471)     P----LAVLKGFRNLPTGMPSVLLIVTGLTWLSWFPFILYDTDWMGREIYHGDPKGTDPQI
SEQ ID NO:27 (gi 542020)      ----GEILGAFKNLKRPMWILLLVTCLNWIAWFPFLLFDTDWMGREVYGGDSSGSAEQL
SEQ ID NO:28 (gi 1935019)     ----GQLSGAFKELKRPMWILLLVTCLNWIAWFPFLLFDTDWMGKEVYGGTVGEGHA-
SEQ ID NO:2                   P----LAVLKGFKDLPPGMPSVLLVTAITWLSWFPFILYDTDWMGREIYHGDPKGSNAQI
SEQ ID NO:4                   ------------------------------------------------------------
SEQ ID NO:6                   P----LAVLKGFKNLPTGMPSVLLVTGLTWLSWFPFILYDTDWMGREIYHGDPKGSNAQI
SEQ ID NO:8                   ----LWELFGSFRYFTLPVMVLIVTALTWIGWFPFILFDTDWMGREIYRGSPDDPSITQ
SEQ ID NO:10                  PGAVLVNILTSMRHLPPGMYSVLLVMALTWLSWFPFFLFDTDWMGREVYHGDPNGNLSER
SEQ ID NO:12                  ----CGELCLAFKGLKRPMWMLMLVTAVNWIAWFPYFLFDTDWMGREVYGGDVGQ---
SEQ ID NO:14                  ----GQLFGAFRELKRPMWILLLVTCLNWDCLVPFLLFDTDWD----------------
SEQ ID NO:16                  ------------------------------------------------------------
SEQ ID NO:18                  --------AGMPSVLLVTGLTWLSWFPFILYDTDWMGREIYHGDPKGTPDEA
SEQ ID NO:20                  P----LAVFKGFKNLPP-.MPSVLLVTGLTWLSWFPFIIYDTDWMGREIYHGDPKGTPDE
SEQ ID NO:22                  P----LAVFKGFKNLPPGMPSVLLVTGLTWLSWFPFIIYDTDWMGREIYHGDPKGTPDEA
SEQ ID NO:24                  PGAVLVKILTSMRHLPPGMYSVLLVMALTWLSWFPFFLFDTDWMGREVYHGDPKGNASER 421                                                               480
SEQ ID NO:25 (gi 2969887)     S---YSDGVRMCAFGLMMNSVVLGITSVLMEKLCRIWGSG-FMWGLSNILMTICF-FAML
SEQ ID NO:26 (gi 2723471)     --EAFNQGVRAGAFGLLNSIVLGFSSFLIEPMCRKVGP-RVVWVTSNFLVCIAMAATAL
SEQ ID NO:27 (gi 542020)      --KLYDRGVRAGALGLMNSVVLGFTSLGVEVLARGVGGVKRLWGIVNFVLAVCLAMTVL
SEQ ID NO:28 (gi 1935019)     ----YDMGVREGALGLMNSVVLGATSLGVDILARGVGGVKRLWGIVNFLLAICLGLTVL
SEQ ID NO:2                   --SAFNEGVRVGAFGLLNSVILGFSSFLIEPMCRKVGP-RVVWVTSNFMVCVAMAATAL
SEQ ID NO:4                   --SAFDEGVRVGSFGLLNSIVLGFSSFLIEPMCRKVGP-RVVWVTSNFMVCVAMAATAL
SEQ ID NO:6                   S---YHDGVRMGSFG-MLNSVLLGFTSIVLEKLCRKWGAG-LVWGVSNIIMALCF-VAML
SEQ ID NO:8                   --KAYDNGVREGAFGLLLNSVVLGFLVDPLCRLMGA-RLVWAISNFTVFICMLATAI
SEQ ID NO:10                  --KAYDSGVHAGSLGLMNAVVLAVMSLAIEPLGRVVGGIKWLWGIVNILLAICLGMTVL
SEQ ID NO:12                  ----WGVR-------CTE--
SEQ ID NO:14                  ------------------------------------------------------------
SEQ ID NO:16                  ----LGGVKRLWGGINFLLAVCLAMTVV
SEQ ID NO:18                  --NAFQAGVRAGAFGLLNSVVLGFSSFLIEPLCKRLGP-RVVWVSSNFLVCISMAAICI
SEQ ID NO:20                  --ANAFQAGVRAGAFGLLLNSVVLGFSSFLIEPLCKRLG-PRVVWVSSNFLVCLSMAAIC
SEQ ID NO:22                  --NAFQAGVRAGAFGLLNSVVLGFSSFLIEPLCKRLGP-RVVWVSSNFLVCLSMAAICI
SEQ ID NO:24                  --KAYDDGVREGAFGLLLNSVVLGIGSFLIDPLCRMIGA-RLVWAISNFTVFACMLATTI
```

FIGURE 1E

```
                          481                                                                   540
SEQ ID NO:25  (gi 2969887)  LITFIAKNMDYGTNP-------PPNGIVISALIVFAILGIPLAITYSVPYALVSTRIES
SEQ ID NO:26  (gi 2723471)  ISFWSLKDFH-----GTVQKAITADKSIKAVCLVLFAFLGVPLAVLYSVFFAVTAQLAAT
SEQ ID NO:27  (gi 542020)   VTKQAESTRRFATVSGGAKVPLPPSGVKAGALALFAVMGVPQAITYSIPFALASIFSNT
SEQ ID NO:28  (gi 1935019)  VTKLAQHSRQYAPGTGALGDPLPPSEGIKAGALTLFSVLGVPLAITYSIPFALASIFSST
SEQ ID NO:2                 ISFSLRDYH------GYVQDAITANASIKAVCLVLFAFLGVPLAILYSVPFAVTAQLAAT
SEQ ID NO:4                 LSWISSDLYS-----SKLHHIGANKTVKITALVVFSLLGLPLSITYSVPFSVTAELTAG
SEQ ID NO:6                 ISFWSLKDYH-----GYVQDAITASTSIKAVCLVLFAFLGVPLAILYSVPFAVTAQLAAT
SEQ ID NO:8                 VITYVAKNMDYPPSGV------PPTGIVIASIVFTILGAPLAITYSIPYAMAASRVEN
SEQ ID NO:10                LSWISFDLYS-----SKLHHIGANKTVKNSALIVFSLLGLPLSITYSVPFSVTAELTAG
SEQ ID NO:12                ITKIAEHERLLNPALVGN-----FSLGIKVGSMVFFSVLGIPLAITFSVPFALASIYSST
SEQ ID NO:14                -GKXGER-KGYDKG-------------------------------------------
SEQ ID NO:16                VTKMADSERQFKTLPDGSKTALPPGDIKAGALSIFAVLGAPLAVTFSVPCALASIFSNS
SEQ ID NO:18                ISWWATQDLH-----GYIQHAITASKEIKIVSLALFAFLGIPLAILYSVPFAVTAQLAAN
SEQ ID NO:20                IISWWATQDLH-----HGYIQHAITASKEIKIVSLALFAFLGIPLAILYSVTFAVTAQLAA
SEQ ID NO:22                ISWWATQDLH-----GYIQHAITASKEIKIVSLALFAFLGIPLAILYSVTFAVTAQLAAN
SEQ ID NO:24                LSWISYDLYS-----SKLQHIVGADKTVKTSALILFSLLGLPLSITYSVPFSVTAELTAG 541                                                                   600
SEQ ID NO:25  (gi 2969887)  LGLGQGLSMGVLNLAIVVPQVIVSLGSGPWDQLFGGGNSPAFVVAALSAFAAGLIALIAI
SEQ ID NO:26  (gi 2723471)  RGGGQGLCTGVLNISTVIPQVVIALGAGPWDELFGKGNIPAFGLASGFALIGGVAGIFLL
SEQ ID NO:27  (gi 542020)   SGAGQGLSLGVLNLSIVIPQMIVSVAAGPWDALFGGGNLPAFVVGAVAALASGIFALTML
SEQ ID NO:28  (gi 1935019)  SGAGQGLSLGVLNLAIVIPQMFVSVLSGPWDALFGGGNLPAFVVGAVAALASGILSIIL
SEQ ID NO:2                 RGGGQGLCTGVLNISIVIPQVIIALGAGPMDALFGKGNIPAFGVASAFALVGGVVGVFLL
SEQ ID NO:4                 TGGGQGLCTGVLATGVLNISIVIPQVIVSLGAGPMDALYGGGNTPAFVLASVFSLAAGVLAVLKL
SEQ ID NO:6                 KGGGQGLCTGVLNISIVIPQVIIALGAGPWDALFGKGNIPAFGVASGFALIGGVVGVFLL
SEQ ID NO:8                 LGLGQGLAMGIILNLAIVIPQVIVSLGSGPMDFGGGNAPAFAVAAAASFIGGLVAILGL
SEQ ID NO:10                TGGGQGLATGVLNLAIVVPQVIVSLGAGPWDALFGGGNVPAFALASVFSLGAGVLAVIKL
SEQ ID NO:12                SGAGQGLSLGVLNIAIVVPQMIVSTSGPWDALFGGGNLPAFVLGAVAAVVSAILAVLLL
SEQ ID NO:14                ----------------------------------------------------------
SEQ ID NO:16                SGAGQGLSLGVLNLAIVIPQMEVSVLSGPWDALFGGGNLPAFVVGAISAAVSGILSFTML
SEQ ID NO:18                RGGGQGLCTGVLNIAIVIPQVIIAVGAGPMDELFGKGNIPAFGVASAFALIGGIVGIFLL
SEQ ID NO:20                KRGGGQGLCTGVLNIAIVIPQVIIAVGAGPMDELFGKGNIPAFGMASAFALIGGIVGIFL
SEQ ID NO:22                RCGGQWLCTGVLNIAIAIPQVIIAGAGPWDELFGKGNIPAFGVASAFALIGGIVGIFLL
SEQ ID NO:24                TGGGQGLATGVLNLAIVAPQIVVSLGAGPWDKLLGGNVPAFALASVFSLAAGVLAVIKL
```

FIGURE 1F

```
                              601                      621
SEQ ID NO:25 (gi 2969887)     RRPRVD-KSRLH--------H--
SEQ ID NO:26 (gi 2723471)     PKISK----RQFWSVSMGGGH--
SEQ ID NO:27 (gi 542020)      PSPQPDMP-SAKALT-AAFH---
SEQ ID NO:28 (gi 1935019)     PSPPPDMAKSVSATG-GGFH---
SEQ ID NO:2                   PKISK----RQFRAVS-AGGH--
SEQ ID NO:4                   PKLSN----S-YQSAGFHGFG--
SEQ ID NO:6                   PKISK----RQFRAVS-AGGH--
SEQ ID NO:8                   PRARIASRRRGH--------R--
SEQ ID NO:10                  PKLPN----S-YRSAGFHGFG--
SEQ ID NO:12                  PTPKKADEVRASSLNMGSLH---
SEQ ID NO:14                  ------------------FR---
SEQ ID NO:16                  PSPPPDVVLSK--VSGGGMH---
SEQ ID NO:18                  PKISR----RQFRAVS-GGGH--
SEQ ID NO:20                  LPKIS----RRQFRAV-SGGGH
SEQ ID NO:22                  PKISR----LQFRAVS-GGGH--
SEQ ID NO:24                  PKLSN----N-YQSAGFH-MG--
```

NUCLEIC ACID MOLECULES ENCODING A WHEAT SUCROSE TRANSPORTER

This application claims the benefit of U.S. Provisional Application No. 60/081,148, filed Apr. 9, 1998.

FIELD OF THE INVENTION

This invention is in the field of plant molecular biology. More specifically, this invention pertains to nucleic acid fragments encoding sucrose transport proteins in plants and seeds.

BACKGROUND OF THE INVENTION

Sucrose is the first form of carbohydrate to leave photosynthesizing cells in most higher plants and is the main form of transported carbon in most annual field crops plants such as corn, soybeans and wheat. As such its movement and concentration across various plant membranes is critical to plant growth and development. In addition sucrose is the main form of carbon that moves into developing seeds of soybeans, corn and wheat. This movement and concentration is accomplished by the action of sucrose carrier proteins that act to move sucrose against a concentration gradient by coupling sucrose movement to the opposite vectoral movement of a proton. Specific sucrose carrier sequences from these crop plants should find use in controlling the timing and extent of phenomena such as grain fill duration that are important factors in crop yield and quality. Accordingly, the availability of nucleic acid sequences encoding all or a portion of these enzymes would facilitate studies to better understand carbohydrate metabolism and function in plants, provide genetic tools for the manipulation of these biosynthetic pathways, and provide a means to control carbohydrate transport and distribution in plant cells.

SUMMARY OF THE INVENTION

The instant invention relates to isolated nucleic acid fragments encoding proteins involved in sucrose transport. Specifically, this invention concerns an isolated nucleic acid fragment encoding a sucrose transport protein. In addition, this invention relates to a nucleic acid fragment that is complementary to the nucleic acid fragment encoding the sucrose transport protein. An additional embodiment of the instant invention pertains to a polypeptide encoding all or a substantial portion of a sucrose transport protein.

In another embodiment, the instant invention relates to a chimeric gene encoding a sucrose transport protein, or to a chimeric gene that comprises a nucleic acid fragment that is complementary to a nucleic acid fragment encoding a sucrose transport protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a sucrose transport protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a sucrose transport protein in a transformed host cell comprising: a) transforming a host cell with a chimeric gene comprising a nucleic acid fragment encoding a sucrose transport protein; and b) growing the transformed host cell under conditions that are suitable for expression of the chimeric gene wherein expression of the chimeric gene results in production of altered levels of sucrose transport protein in the transformed host cell.

An addition embodiment of the instant invention concerns a method for obtaining a nucleic acid fragment encoding all or a substantial portion of an amino acid sequence encoding a sucrose transport protein.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1A-FIG. 1F shows a comparison of the amino acid sequences set forth in SEQ ID NOs:2, 4, 6, 8, 10, 12, 14, 16, 18, 20, 22 and 24 and the *Daucus carota* (SEQ ID NO:25), *Oryza sativa* (SEQ ID NO:26), *Ricinus communis* (SEQ ID NO:27) and *Vicia faba* (SEQ ID NO:28) sucrose transport protein amino acid sequences.

The following sequence descriptions and sequence listings attached hereto comply with the rules governing nucleotide and/or amino acid sequence disclosures in patent applications as set forth in 37 C.F.R. §1.821-1.825.

SEQ ID NO:1 is the nucleotide sequence comprising the entire cDNA insert in clone cepe7.pk0015.d10 encoding an entire corn sucrose transport protein.

SEQ ID NO:2 is the deduced amino acid sequence of a sucrose transport protein derived from the nucleotide sequence of SEQ ID NO:1.

SEQ ID NO:3 is the nucleotide sequence comprising a portion of the cDNA insert in clone cr1n.pk0075.f5 encoding a portion of a corn sucrose transport protein.

SEQ ID NO:4 is the deduced amino acid sequence of a portion of a sucrose transport protein derived from the nucleotide sequence of SEQ ID NO:3.

SEQ ID NO:5 is the nucleotide sequence comprising a portion of the cDNA insert in clone cr1n.pk0095.c10 encoding a portion of a corn sucrose transport protein.

SEQ ID NO:6 is the deduced amino acid sequence of a portion of a sucrose transport protein derived from the nucleotide sequence of SEQ ID NO:5.

SEQ ID NO:7 is the nucleotide sequence comprising the entire cDNA insert in clone r1r2.pk0043.b1 encoding a portion of a rice sucrose transport protein.

SEQ ID NO:8 is the deduced amino acid sequence of a portion of a sucrose transport protein derived from the nucleotide sequence of SEQ ID NO:7.

SEQ ID NO:9 is the nucleotide sequence comprising the entire cDNA insert in clone r1s6.pk0076.e2 encoding an entire rice sucrose transport protein.

SEQ ID NO:10 is the deduced amino acid sequence of a sucrose transport protein derived from the nucleotide sequence of SEQ ID NO:9.

SEQ ID NO: 11 is the nucleotide sequence comprising the entire cDNA insert in clone sfl1.pk0001.g1 encoding an entire soybean sucrose transport protein.

SEQ ID NO:12 is the deduced amino acid sequence of a sucrose transport protein derived from the nucleotide sequence of SEQ ID NO:11.

SEQ ID NO:13 is the nucleotide sequence comprising a contig assembled from the cDNA inserts in clones sfl1.pk0043.c7 and sdp3c.pk012.c13 encoding a portion of a soybean sucrose transport protein.

SEQ ID NO:14 is the deduced amino acid sequence of a portion of a sucrose transport protein derived from the nucleotide sequence of SEQ ID NO:13.

SEQ ID NO:15 is the nucleotide sequence comprising a portion of the cDNA insert in clone vs1n.pk0002.h3 encoding a portion of a *Vernonia* sucrose transport protein.

SEQ ID NO:16 is the deduced amino acid sequence of a portion of a sucrose transport protein derived from the nucleotide sequence of SEQ ID NO:15.

SEQ ID NO:17 is the nucleotide sequence comprising the entire cDNA insert in clone w1e1n.pk0007.h8 encoding a portion of a wheat sucrose transport protein.

SEQ ID NO:18 is the deduced amino acid sequence of a portion of a sucrose transport protein derived from the nucleotide sequence of SEQ ID NO:17.

SEQ ID NO:19 is the nucleotide sequence comprising the entire cDNA insert in clone w1e1n.pk0103.c11 encoding an entire wheat sucrose transport protein.

SEQ ID NO:20 is the deduced amino acid sequence of a sucrose transport protein derived from the nucleotide sequence of SEQ ID NO:19.

SEQ ID NO:21 is the nucleotide sequence comprising the entire cDNA insert in clone w1m24.pk0015.g11 encoding an entire wheat sucrose transport protein.

SEQ ID NO:22 is the deduced amino acid sequence of a sucrose transport protein derived from the nucleotide sequence of SEQ ID NO:21.

SEQ ID NO:23 is the nucleotide sequence comprising the entire cDNA insert in clone w1mk1.pk0002.e11 encoding an entire wheat sucrose transport protein.

SEQ ID NO:24 is the deduced amino acid sequence of a sucrose transport protein derived from the nucleotide sequence of SEQ ID NO:23.

SEQ ID NO:25 is the amino acid sequence of a *Daucus carota* sucrose transport protein (NCBI Identifier No. gi 2969887).

SEQ ID NO:26 is the amino acid sequence of a *Oryza sativa* sucrose transport protein (NCBI Identifier No. gi 2723471).

SEQ ID NO:27 is the amino acid sequence of a *Ricinus communis* sucrose transport protein (NCBI Identifier No. gi 542020).

SEQ ID NO:28 is the amino acid sequence of a *Vicia faba* sucrose transport protein (NCBI Identifier No. gi 1935019).

The Sequence Listing contains the one letter code for nucleotide sequence characters and the three letter codes for amino acids as defined in conformity with the IUPAC-IUBMB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence. As used herein, "substantially similar" refers to nucleic acid fragments wherein changes in one or more nucleotide bases results in substitution of one or more amino acids, but do not affect the functional properties of the protein encoded by the DNA sequence.

"Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS.* 5:151-153) with the default parameters (GAP PENALTY=10, GAP LENGTH PENALTY=10), (hereafter Clustal algorithm). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403-410. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the sucrose transport proteins as set forth in SEQ ID NOs:2, 4, 6, 8, 10, 12, 14, 16, 18, 20, 22 and 24. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945, 050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sucrose transport proteins have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Sucrose Transport Proteins

| Enzyme | Clone | Plant |
| --- | --- | --- |
| Sucrose Transporter | cepe7.pk0015.d10 | Corn |
| | cr1n.pk0095.c10 | Corn |
| | cr1n.pk0075.f5 | Corn |
| | rlr2.pk0043.b1 | Rice |
| | rls6.pk0076.e2 | Rice |
| | sfl1.pk0001.g1 | Soybean |
| | sfl1.pk0043.c7 | Soybean |
| | sdp3c.pk012.c13 | Soybean |
| | vs1n.pk0002.h3 | *Vernonia* |
| | wle1n.pk0007.h8 | Wheat |
| | wle1n.pk0103.c11 | Wheat |
| | wlm24.pk0015.g11 | Wheat |
| | wlmk1.pk0002.e11 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other sucrose transport proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed sucrose transport proteins are present at higher or lower levels than normal or in cell types or developmental stages in which they are not normally found. This would have the effect of altering the level of sucrose metabolism in those cells.

Overexpression of the sucrose transport proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant sucrose transport proteins to different cellular compartments, or to facilitate its secretion from the cell. It is thus envisioned that the chimeric gene described above may be further supplemented by altering the coding sequence to encode a sucrose transport protein with appropriate intracellular targeting sequences such as transit sequences (Keegstra, K. (1989) *Cell* 56:247-253), signal sequences or sequences encoding endoplasmic reticulum localization (Chrispeels, J. J., (1991) *Ann. Rev. Plant Phys. Plant Mol. Biol.* 42:21-53), or nuclear localization signals (Raikhel, N. (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding sucrose transport proteins in plants for some applications. In order to accomplish this, a chimeric gene designed for co-suppression of the instant sucrose transport proteins can be constructed by linking a gene or gene fragment encoding a sucrose transport protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant sucrose transport proteins (or portions thereof) may be produced in heterologous host cells, particularly in the cells of microbial hosts, and can be used to prepare antibodies to the these proteins by methods well known to those skilled in the art. The antibodies are useful for detecting sucrose transport proteins in situ in cells or in vitro in cell extracts. Preferred heterologous host cells for production of the instant sucrose transport proteins are microbial hosts. Microbial expression systems and expression vectors containing regulatory sequences that direct high level expression of foreign proteins are well known to those skilled in the art. Any of these could be used to construct a chimeric gene for production of the instant sucrose transport proteins. This chimeric gene could then be introduced into appropriate microorganisms via transformation to provide high level expression of the encoded sucrose transport protein. An example of a vector for high level expression of the instant sucrose transport proteins in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) Genomics 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314-331).

The production and use of plant gene-derived probes for use in genetic mapping is described in R. Bernatzky, R. and Tanksley, S. D. (1986) *Plant Mol. Biol. Reporter* 4(1):37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149-154). Although current methods of FISH mapping favor use of large clones (several to several hundred KB; see Laan, M. et al. (1995) *Genome Research* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95-96), polymorphism of PCR-amplified fragments (CAPS; Sheffield, V. C. et al. (1993) *Genomics* 16:325-332), allele-specific ligation (Landegren, U. et al. (1988) *Science* 241:1077-1080), nucleotide extension reactions (Sokolov, B. P. (1990) *Nucleic Acid Res.* 18:3671), Radiation Hybrid Mapping (Walter, M. A. et al. (1997) *Nature Genetics* 7:22-28) and Happy Mapping (Dear, P. H. and Cook, P. R. (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the sucrose transport protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a sucrose transport protein can be identified and obtained. This mutant plant can then be used to determine or confirm the natural function of the sucrose transport protein gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, *Vernonia* and wheat tissues were prepared. The characteristics of the libraries are described below.

TABLE 2 cDNA Libraries from Corn Rice, Soybean *Vernonia* and Wheat

| Library | Tissue | Clone |
|---|---|---|
| cepe7 | Corn epicotyl from 7 day old etiolated seedling | cepe7.pk0015.d10 |
| cr1n | Corn root from 7 day seedling grown in light* | cr1n.pk0075.f5 cr1n.pk0095.c10 |
| rlr2 | Rice leaf 15 days after germination 2 hours after infection of strain *Magnaporthe grisea* 4360-R-62 (AVR2-YAMO) | rlr2.pk0043.b1 |
| rls6 | Rice leaf 15 days after germination 6 hours after infection of strain *Magnaporthe grisea* 4360-R-62 (AVR2-YAMO) | rls6.pk0076.e2 |
| sdp3c | Soybean developing pods 8-9 mm | sdp3c.pk012.c13 |
| sfl1 | Soybean immature flower | sfl1.pk0001.g1 sfl1.pk0043.c7 |
| vs1 | *Vernonia* developing seed | vs1n.pk0002.h3 |
| wle1n | Wheat leaf 7 day old etiolated seedling light grown* | wle1n.pk0007.h8 wle1n.pk0103.c11 |
| wlm24 | Wheat seedling 24 hours after inoculation with *Erysiphe graminis* | wlm24.pk0015.g11 |

TABLE 2-continued cDNA Libraries from Corn Rice, Soybean *Vernonia* and Wheat

| Library | Tissue | Clone |
|---|---|---|
| wlmk1 | Wheat seedlings 1 hour after inoculation with *Erysiphe graminis* and treatment with fungicide** | wlmk1.pk0002.e11 |

*These libraries were normalized essentially as described in U.S. Pat. No. 5,482,845
**Application of 6-iodo-2-propoxy-3-propyl-4(3H)-quinazolinone; synthesis and methods of using this compound are described in U.S. Ser. No. 08/545,827, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding sucrose transport proteins were identified by conducting BLAST (Basic Local Alignment Search Tool; Altschul, S. F., et al., (1993) *J. Mol. Biol.* 215:403-410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266-272 and Altschul, Stephen F., et al. (1997) *Nucleic Acids Res.* 25:3389-3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Sucrose Transporter Proteins

The BLASTX search using the EST sequences from clones cepe7.pk0015.d10, cr1n.pk0095.c10, cr1n.pk0075.f5, r1s6.pk0076.e2, w1e1n.pk0007.h8, w1e1n.pk0007.h8, w1e1n.pk0103.c11, w1m24.pk0015.g11 and w1mk1.pk0002.e11 revealed similarity of the proteins encoded by the cDNAs to a sucrose transporter from *Oryza sativa* (NCBI Identifier No. gi 2723471). The BLASTX search using the EST sequence from clone r1r2.pk0043.b1 revealed similarity of the protein encoded by the cDNA to a sucrose transporter from *Daucus carota* (NCBI Identifier No. gi 2969887). The BLASTX search using the EST sequence from clone sfl1.pk0001.g1 revealed similarity of the protein encoded by the cDNA to a sucrose transporter from *Vicia faba* (NCBI Identifier No. gi 1935019). The BLASTX search using the EST sequences from clones sfl1.pk0043.c7, sdp3c.pk012.c13 and vs1n.pk0002.h3 revealed similarity of the proteins encoded by the cDNAs to a sucrose transporter from *Ricinus communis* (NCBI Identifier No. gi 542020).

In the process of comparing the ESTs it was found that soybean clones sfl1.pk0043.c7 and sdp3c.pk012.c13 had overlapping regions of homology. Using this homology it was possible to align the ESTs and assemble a contig encoding a unique soybean sucrose transport protein.

The BLAST results for each of these ESTs and the soybean contig are shown in Table 3:

TABLE 3

BLAST Results for Clones Encoding Polypeptides Homologous to *Daucus carota*, *Oryza sativa*, *Ricinus communis* and *Vicia faba* Sucrose Transport Proteins

| Clone | BLAST pLog Score |
|---|---|
| cepe7.pk0005.d10 | >250.00 |
| cr1n.pk0095.c10 | >250.00 |
| cr1n.pk0075.f5 | 31.10 |
| rlr2.pk0043.b1 | 148.00 |
| r1s6.pk0076.e2 | >250.00 |
| sfl1.pk0001.g1 | >250.00 |
| Contig composed of: sfl1.pk0043.c7 sdp3c.pk012.c13 | 142.00 |
| vs1n.pk0002.h3 | 59.30 |
| w1e1n.pk0007.h8 | 110.00 |
| w1e1n.pk0103.c11 | >250.00 |
| w1m24.pk0015.g11 | >250.00 |
| w1mk1.pk0002.e11 | 177.00 |

The sequence of a portion of the cDNA insert from clone cepe7.pk0015.d10 is shown in SEQ ID NO:1; the deduced amino acid sequence of this cDNA, which represents 100% of the protein, is shown in SEQ ID NO:2. A calculation of the percent similarity of the amino acid sequence set forth in SEQ ID NO:2 and the *Oryza sativa* sequence (using the Clustal algorithm) revealed that the protein encoded by SEQ ID NO:2 is 82% similar to the *Oryza sativa* protein.

The sequence of a portion of the cDNA insert from clone cr1n.pk0075.f5 is shown in SEQ ID NO:3; the deduced amino acid sequence of this cDNA, which represents 93% of the protein, is shown in SEQ ID NO:4. A calculation of the percent similarity of the amino acid sequence set forth in SEQ ID NO:4 and the *Oryza sativa* sequence (using the Clustal algorithm) revealed that the protein encoded by SEQ ID NO:4 is 50% similar to the *Oryza sativa* protein.

The sequence of a portion of the cDNA insert from clone cr1n.pk0095.c10 is shown in SEQ ID NO:5; the deduced amino acid sequence of this cDNA, which represents 20% of the protein (C-terminal region), is shown in SEQ ID NO:6. A calculation of the percent similarity of the amino acid sequence set forth in SEQ ID NO:6 and the *Oryza sativa* sequence (using the Clustal algorithm) revealed that the protein encoded by SEQ ID NO:6 is 86% similar to the *Oryza sativa* protein.

The sequence of a portion of the cDNA insert from clone r1r2.pk0043.b1 is shown in SEQ ID NO:7; the deduced amino acid sequence of this cDNA, which represents 79% of the protein (C-terminal region), is shown in SEQ ID NO:8. A calculation of the percent similarity of the amino acid sequence set forth in SEQ ID NO:8 and the *Daucus carota* sequence (using the Clustal algorithm) revealed that the protein encoded by SEQ ID NO:8 is 60% similar to the *Daucus carota* protein.

The sequence of a portion of the cDNA insert from clone r1s6.pk0076.e2 is shown in SEQ ID NO:9; the deduced amino acid sequence of this cDNA, which represents 100% of the protein, is shown in SEQ ID NO:10. A calculation of the percent similarity of the amino acid sequence set forth in SEQ ID NO:10 and the *Oryza sativa* sequence (using the Clustal algorithm) revealed that the protein encoded by SEQ ID NO:10 is 55% similar to the *Oryza sativa* protein. Due to a percent similarity of only 55% with a known rice sucrose transport protein clone r1s6.pk0076.e2 appears to represent a second rice sucrose transport protein.

The sequence of a portion of the cDNA insert from clone sfl1.pk0001.g1 is shown in SEQ ID NO: 11; the deduced amino acid sequence of this cDNA, which represents 100% of the protein, is shown in SEQ ID NO:12. A calculation of the percent similarity of the amino acid sequence set forth in SEQ ID NO:12 and the *Vicia faba* sequence (using the Clustal algorithm) revealed that the protein encoded by SEQ ID NO:12 is 67% similar to the *Vicia faba* protein.

The sequence of a portion of the contig composed of clones sfl1.pk0043.c7 and sdp3c.pk012.c13 is shown in SEQ ID NO:13; the deduced amino acid sequence of this contig, which represents 62% of the protein (N-terminal region), is shown in SEQ ID NO:14. A calculation of the percent similarity of the amino acid sequence set forth in SEQ ID NO:14 and the *Ricinus communis* sequence (using the Clustal algorithm) revealed that the protein encoded by SEQ ID NO:14 is 66% similar to the *Ricinus communes* protein.

The sequence of a portion of the cDNA insert from clone vs1n.pk0002.h3 is shown in SEQ ID NO:15; the deduced amino acid sequence of this cDNA, which represents 31% of the protein (C-terminal region), is shown in SEQ ID NO:16. A calculation of the percent similarity of the amino acid sequence set forth in SEQ ID NO:16 and the *Ricinus communes* sequence (using the Clustal algorithm) revealed that the protein encoded by SEQ ID NO:16 is 66% similar to the *Ricinus communes* protein.

The sequence of a portion of the cDNA insert from clone w1e1n.pk0007.h8 is shown in SEQ ID NO:17; the deduced amino acid sequence of this cDNA, which represents 43% of the protein (C-terminal region), is shown in SEQ ID NO:18. A calculation of the percent similarity of the amino acid sequence set forth in SEQ ID NO:18 and the *Oryza sativa* sequence (using the Clustal algorithm) revealed that the protein encoded by SEQ ID NO:18 is 80% similar to the *Oryza sativa* protein.

The sequence of a portion of the cDNA insert from clone w1e1n.pk0103.c11 is shown in SEQ ID NO:19; the deduced amino acid sequence of this cDNA, which represents 100% of the protein, is shown in SEQ ID NO:20. A calculation of the percent similarity of the amino acid sequence set forth in SEQ ID NO:20 and the *Oryza sativa* sequence (using the Clustal algorithm) revealed that the protein encoded by SEQ ID NO:20 is 80% similar to the *Oryza sativa* protein.

The sequence of a portion of the cDNA insert from clone w1m24.pk0015.g11 is shown in SEQ ID NO:21; the deduced amino acid sequence of this cDNA, which represents 100% of the protein, is shown in SEQ ID NO:22. A calculation of the percent similarity of the amino acid sequence set forth in SEQ ID NO:22 and the *Oryza sativa* sequence (using the Clustal algorithm) revealed that the protein encoded by SEQ ID NO:22 is 80% similar to the *Oryza sativa* protein.

The sequence of a portion of the cDNA insert from clone w1mk1.pk0002.e11 is shown in SEQ ID NO:23; the deduced amino acid sequence of this cDNA, which represents 97% of the protein, is shown in SEQ ID NO:24. A calculation of the percent similarity of the amino acid sequence set forth in SEQ ID NO:24 and the *Oryza sativa* sequence (using the Clustal algorithm) revealed that the protein encoded by SEQ ID NO:24 is 54% similar to the *Oryza sativa* protein.

The percent similarity between each of the corn, rice, soybean, *Vernonia* and wheat amino acid sequence was calculated to range from 12 to 98% using the Clustal algorithm. FIG. 1A-FIG. 1F presents an alignment of the amino acid sequences set forth in SEQ ID NOs:2, 4, 6, 8, 10, 12, 14, 16, 18, 20, 22 and 24 and the *Daucus carota, Oryza sativa, Ricinus communis* and *Vicia faba* sucrose transport protein amino acid sequences.

BLAST scores and probabilities indicate that the instant nucleic acid fragments encode entire or portions of proteins. These sequences represent the first corn, soybean and wheat, amino acid sequences and a new rice sequence encoding sucrose transport proteins.

Example 4

Expression of Chimeric Genes in Monocot Cells

A chimeric gene comprising a cDNA encoding a sucrose transport protein in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a sucrose transport protein, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al., (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833-839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant sucrose transport proteins in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising a sequence encoding a sucrose transport protein. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al.

(1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the sucrose transport protein and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl₂ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant sucrose transport proteins can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the sucrose transport protein are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having sucrose transport activity, wherein the polypeptide has an amino acid sequence of at least 95% sequence identity, based on the Clustal method of alignment, when compared to SEQ ID NO:20, or;
   (b) a complement of the nucleotide sequence of (a), wherein the complement and the nucleotide sequence consist of the same number of nucleotides and are 100% complementary.

2. The polynucleotide of claim 1 wherein the nucleotide sequence comprises SEQ ID NO:19.

3. A recombinant DNA construct comprising the polynucleotide of claim 1 operably linked to at least one regulatory sequence.

4. A transformed host cell comprising the recombinant DNA construct of claim 3.

5. A method of altering the level of expression of a sucrose transport protein in a host cell comprising:
   (a) transforming a host cell with the recombinant DNA construct of claim 3; and
   (b) growing the transformed host cell produced in step (a) under conditions that are suitable for expression of the recombinant DNA construct
wherein expression of the recombinant DNA construct results in production of altered levels of a sucrose transport protein in the transformed host cell.

6. A plant comprising the recombinant DNA construct of claim 3.

\* \* \* \* \*

UNITED STATES PATENT AND TRADEMARK OFFICE
CERTIFICATE OF CORRECTION

PATENT NO. : 7,605,247 B1
APPLICATION NO. : 11/901765
DATED : October 20, 2009
INVENTOR(S) : Stephen M. Allen, William D. Hitz and J. Antoni Rafalski It is certified that error appears in the above-identified patent and that said Letters Patent is hereby corrected as shown below:

On the Title Page
Item (73), Assignee, change "E. I. du Point de Nemours and Company" to read
-- E. I. du Pont de Nemours and Company --.

Signed and Sealed this

Twenty-second Day of June, 2010

David J. Kappos
*Director of the United States Patent and Trademark Office*

SEQUENCE LISTING

<160> NUMBER OF SEQ ID NOS: 28

<210> SEQ ID NO 1
<211> LENGTH: 2088
<212> TYPE: DNA
<213> ORGANISM: Zea mays

<400> SEQUENCE: 1

-continued

| | |
|---|---|
| gcacgagaca ctcctcacct ctcctcgctc cacgcacgcg ctctctcacc cgctggctat | 60 |
| tagtcgtcgt cccttggatt tcgacactct ctctagcggg cgcctgttcc gccgccgtcc | 120 |
| atcgatccta gctagctagc tagctagggc gcgaccgtcg tctcggtggt tgttgacagg | 180 |
| tcccgtacgt gtgtgctcgc catggctcgt ggcgacggcg ggcagctggc ggagctgtcc | 240 |
| gcggggtcc gcggcgcggc cgcggtggtg gaccacgtgg ccccgatcag cctcgggagg | 300 |
| ctcatcctcg ccggcatggt cgccggcggc gtgcagtacg gctgggcgct gcagctctcc | 360 |
| ctcctcacgc cctacgtgca gactctgggg ctttcacatg cgctcacttc attcatgtgg | 420 |
| ctctgcggcc ctattgccgg cttagtggtc caaccgctgg ttggcctgta cagcgacagg | 480 |
| tgtacatcga gatgggggag acggaggccg tttatcctga cagggtgcat gctcatctgc | 540 |
| gttgccgtca ttgttgtcgg attctcgtca gacatcggag ctgctctagg ggacacgaag | 600 |
| gaacactgca gcctctacca cggtcctcgt tggcacgctg cgatcgtgta cgttctgggg | 660 |
| ttttggctcc ttgacttctc caacaacact gtgcagggtc cagcacgtgc tatgatggct | 720 |
| gatctatgtg accatcatgg gccaagtgcg gctaactcca tcttctgttc ttggatggcg | 780 |
| ctgggaaaca tcctaggcta ctcctctggc tccacgaaca attggcacaa gtggtttccc | 840 |
| ttccttaaaa cgagcgcctg ctgtgaggcc tgtgcgaacc tgaaaggtgc atttctggtg | 900 |
| gccgtggtgt tcctagtcct gtgcctgacg gtaaccctga tcttcgccaa ggaggtgccg | 960 |
| tacagagcga acgagaacct cccgacgacg aaggccggcg gcgaggtcga gactgagcct | 1020 |
| accgggccac ttgccgtgct caagggcttc aaggacctgc ctcccgggat gccgtccgtg | 1080 |
| ctcctcgtga ctgccatcac ctggctttcg tggttcccgt tcatcctcta cgacaccgac | 1140 |
| tggatgggcc gggagatcta ccacggcgac cccaagggga gcaacgccca gatctcggcg | 1200 |
| ttcaacgaag gtgtccgagt cggcgcgttc gggctgctac tcaactcggt tattctaggg | 1260 |
| ttcagctcgt tcctgatcga gcccatgtgc cggaaggtcg ggccgagggt ggtgtgggtg | 1320 |
| acgagcaact tcatggtctg cgtcgccatg gcggccaccg cgctgatcag cttctggtcg | 1380 |
| ctcagggact accacgggta cgtgcaggac gccataccg cgaacgccag catcaaggcc | 1440 |
| gtctgcctcg tcctcttcgc cttcctgggc gtccctctcg ccatcctgta cagcgtcccg | 1500 |
| ttcgcggtga cggcgcagct ggcggccacc cggggcggcg ggcaggggct gtgcaccggc | 1560 |
| gtcctcaaca tctccatcgt catccctcag gtgatcatcg cgctgggcgc cggcccgtgg | 1620 |
| gacgcgctgt tcgggaaggg caacatcccg cgcttcggcg tcgcgtcggc cttcgccctc | 1680 |
| gtcggcggcg tcgtgggcgt gttcctgctg cccaagatct ccaagcgcca gttccgggcc | 1740 |
| gtcagcgcgg gcggccactg atcgaacccg gccggggccg gccgccggca cgcagcccgg | 1800 |
| caagagctgt atgttgttga gagttgaaca gaaaccatgc atgtgtgctt ctgtagttct | 1860 |
| gttgtttgtg gtcgatcgat gggcgttgcg tggcagcgtg ggcaagcgag gcgaggtgcg | 1920 |
| cggatccaaa aaagggcca ttcgatcaat caatgtgtag tagagtacaa ctagacgatg | 1980 |
| atgttcacat catttgtctt taatacatac cggtttctat tgtctttaaa aaaaaaaaa | 2040 |
| aaaaaaaaaa aaaaaaaaaa aaaaaaaaaa aaaaaaaaaa aaaaaaaa | 2088 |

<210> SEQ ID NO 2
<211> LENGTH: 519
<212> TYPE: PRT
<213> ORGANISM: Zea mays

<400> SEQUENCE: 2

Met Ala Arg Gly Asp Gly Gly Gln Leu Ala Glu Leu Ser Ala Gly Val

-continued

```
  1               5                 10                15
Arg Gly Ala Ala Ala Val Val Asp His Val Ala Pro Ile Ser Leu Gly
                20                  25                30
Arg Leu Ile Leu Ala Gly Met Val Ala Gly Val Gln Tyr Gly Trp
                35                  40                45
Ala Leu Gln Leu Ser Leu Leu Thr Pro Tyr Val Gln Thr Leu Gly Leu
                50                  55                60
Ser His Ala Leu Thr Ser Phe Met Trp Leu Cys Gly Pro Ile Ala Gly
 65                 70                  75                80
Leu Val Val Gln Pro Leu Val Gly Leu Tyr Ser Asp Arg Cys Thr Ser
                85                  90                95
Arg Trp Gly Arg Arg Pro Phe Ile Leu Thr Gly Cys Met Leu Ile
                100                 105               110
Cys Val Ala Val Ile Val Val Gly Phe Ser Ser Asp Ile Gly Ala Ala
                115                 120               125
Leu Gly Asp Thr Lys Glu His Cys Ser Leu Tyr His Gly Pro Arg Trp
                130                 135               140
His Ala Ala Ile Val Tyr Val Leu Gly Phe Trp Leu Leu Asp Phe Ser
145                 150                 155               160
Asn Asn Thr Val Gln Gly Pro Ala Arg Ala Met Met Ala Asp Leu Cys
                165                 170               175
Asp His His Gly Pro Ser Ala Ala Asn Ser Ile Phe Cys Ser Trp Met
                180                 185               190
Ala Leu Gly Asn Ile Leu Gly Tyr Ser Ser Gly Ser Thr Asn Asn Trp
                195                 200               205
His Lys Trp Phe Pro Phe Leu Lys Thr Ser Ala Cys Cys Glu Ala Cys
                210                 215               220
Ala Asn Leu Lys Gly Ala Phe Leu Val Ala Val Phe Leu Val Leu
225                 230                 235               240
Cys Leu Thr Val Thr Leu Ile Phe Ala Lys Glu Val Pro Tyr Arg Ala
                245                 250               255
Asn Glu Asn Leu Pro Thr Thr Lys Ala Gly Gly Glu Val Glu Thr Glu
                260                 265               270
Pro Thr Gly Pro Leu Ala Val Leu Lys Gly Phe Lys Asp Leu Pro Pro
                275                 280               285
Gly Met Pro Ser Val Leu Leu Val Thr Ala Ile Thr Trp Leu Ser Trp
                290                 295               300
Phe Pro Phe Ile Leu Tyr Asp Thr Asp Trp Met Gly Arg Glu Ile Tyr
305                 310                 315               320
His Gly Asp Pro Lys Gly Ser Asn Ala Gln Ile Ser Ala Phe Asn Glu
                325                 330               335
Gly Val Arg Val Gly Ala Phe Gly Leu Leu Leu Asn Ser Val Ile Leu
                340                 345               350
Gly Phe Ser Ser Phe Leu Ile Glu Pro Met Cys Arg Lys Val Gly Pro
                355                 360               365
Arg Val Val Trp Val Thr Ser Asn Phe Met Val Cys Val Ala Met Ala
                370                 375               380
Ala Thr Ala Leu Ile Ser Phe Trp Ser Leu Arg Asp Tyr His Gly Tyr
385                 390                 395               400
Val Gln Asp Ala Ile Thr Ala Asn Ala Ser Ile Lys Ala Val Cys Leu
                405                 410               415
Val Leu Phe Ala Phe Leu Gly Val Pro Leu Ala Ile Leu Tyr Ser Val
                420                 425               430
```

```
Pro Phe Ala Val Thr Ala Gln Leu Ala Ala Thr Arg Gly Gly Gln
        435                 440                 445

Gly Leu Cys Thr Gly Val Leu Asn Ile Ser Ile Val Ile Pro Gln Val
        450                 455                 460

Ile Ile Ala Leu Gly Ala Gly Pro Trp Asp Ala Leu Phe Gly Lys Gly
465                 470                 475                 480

Asn Ile Pro Ala Phe Gly Val Ala Ser Ala Phe Ala Leu Val Gly Gly
                485                 490                 495

Val Val Gly Val Phe Leu Leu Pro Lys Ile Ser Lys Arg Gln Phe Arg
                500                 505                 510

Ala Val Ser Ala Gly Gly His
        515

<210> SEQ ID NO 3
<211> LENGTH: 825
<212> TYPE: DNA
<213> ORGANISM: Zea mays

<400> SEQUENCE: 3
gcacgagtta agttggatct cttctgatct gtactcaagc aaacttcatc acatcatcgg      60
ggcaaataaa acagtcaaga tcacggcatt ggttgttttc tctcttctcg gattgccact    120
ctccatcact tacagcgttc cgttttctgt gactgctgag ctgactgccg gtacaggagg    180
tggacaaggt ttggccacag gagtcctaaa tcttgctatc gtggttcccc agatagtagt    240
gtcgcttgga gcaggtccat gggacgctct gtatggagga gggaataccc cggcgttcgt    300
cttggcttcg gtcttctccc tggcagcagg tgtgctcgca gttctcaagc tgccaaagct    360
gtccaactcg taccaatctg ccgggttcca tggatttggc tgatgctcat gcccaaaaca    420
cccccgtctg ccatgtaaaa catcacacca acacttggcc ccattttgcc attcgtttac    480
agagaaatga ttcttttttc ctcgtacaac tacagaataa tgacagtgaa agtaggagtt    540
taggtgagag agagagagag gctaggtagg ttgatgtgaa ggtgtaaaag ctgtatcctc    600
cttttttttgt ttttgttttt gttttgtgaca gtgtatgtaa gagctgtcca caagaaaatt    660
tacaagtggt gtaacctgcc ctcgtttgta cattgtacta ctactacatg acaatcatat    720
gtcctttgtc tttatccaag gttgaagacg taaactgagg ccatctatt atcttgggcc     780
atgaaaaaaa aaaaaaaaaa aaaaaaaact cgaaactagt tctct                     825

<210> SEQ ID NO 4
<211> LENGTH: 133
<212> TYPE: PRT
<213> ORGANISM: Zea mays

<400> SEQUENCE: 4

His Glu Leu Ser Trp Ile Ser Ser Asp Leu Tyr Ser Ser Lys Leu His
  1               5                  10                  15

His Ile Ile Gly Ala Asn Lys Thr Val Lys Ile Thr Ala Leu Val Val
                 20                  25                  30

Phe Ser Leu Leu Gly Leu Pro Leu Ser Ile Thr Tyr Ser Val Pro Phe
         35                  40                  45

Ser Val Thr Ala Glu Leu Thr Ala Gly Thr Gly Gly Gln Gly Leu
     50                  55                  60

Ala Thr Gly Val Leu Asn Leu Ala Ile Val Val Pro Gln Ile Val Val
 65                  70                  75                  80

Ser Leu Gly Ala Gly Pro Trp Asp Ala Leu Tyr Gly Gly Gly Asn Thr
```

```
                    85                  90                  95
Pro Ala Phe Val Leu Ala Ser Val Phe Ser Leu Ala Ala Gly Val Leu
            100                 105                 110

Ala Val Leu Lys Leu Pro Lys Leu Ser Asn Ser Tyr Gln Ser Ala Gly
        115                 120                 125

Phe His Gly Phe Gly
    130

<210> SEQ ID NO 5
<211> LENGTH: 1977
<212> TYPE: DNA
<213> ORGANISM: Zea mays

<400> SEQUENCE: 5
gcggcggacc acgtggcgcc gatcagcctc ggcaggctca tcctcgccgg catggtcgcc      60
ggcggcgtgc agtacggctg ggcgctgcag ctctccctcc tcacgcccta cgtgcagact     120
ctggggctct acatgcccct cacttcattc atgtggctat gcggtcctat tgctggctta     180
gtggtccaac cgctggttgg cctgtacagc gataggtgca cagcaagatg gggaagacgc     240
aggccattta tcctgatagg atgcatgctc atctgccttg ccgtcattgt tgttggcttc     300
tcgtccgaca tcgagctgc tctaggggac acaaaggaac actgcagcct ctaccacggc     360
cctcgttggc atgctgcgat cgtgtacgtt ctggggtttt ggctccttga cttctccaac     420
aatactgtgc aaggtccagc gcgtgctatg atggctgatc tgtgcggtca tcatgggcct     480
agtgcagcca actcaatctt ctgttcttgg atggcgctgg gaaacatcct aggctattcc     540
tctggctcca caaacaactg gcacaagtgg tttccgttcc ttatgacaaa cgcgtgctgt     600
gaagcctgcg caaacctgaa aggcgcgttt ctggtggctg tggtgttcct aatcatgtgc     660
ttgactataa ccctgttctt cgccaaggaa gtgccctaca gaggaaacca gaacctcccc     720
acaaaggcaa acggcgaggt cgagactgaa ccttccggcc cactcgctgt gctcaagggc     780
ttcaagaact tgcccacggg gatgccgtcc gtgctcctcg taactggact cacctggctc     840
tcttggttcc cgttcatcct ctacgacacc gactggatgg ccgtgagat ctaccacggc     900 gaccccaagg gtagcaacgc tcagatctcg gcgttcgacg aaggcgtcag agttggctcg     960
ttcgggctgc tgctcaactc gatcgttcta ggattcagct cgttcctgat cgagcccatg    1020
tgccggaagg tcgggccgag ggtggtgtgg gtgacgagca acttcatggt ctgcgtcgcc    1080
atggcggcca ccgcgctgat cagcttctgg tcgctcaagg actaccacgg atacgtgcag    1140
gacgccatca ccgccagcac gagcatcaag gccgtctgcc tcgtcctctt cgcgttcctg    1200
ggtgtccctc tcgccatcct gtacagcgtc ccgttcgcgg tgacggcgca gctggcggcc    1260
acgaagggcg gcgggcaggg gctgtgcacc ggcgtgctca acatctccat cgtcatccct    1320
caggtgatca tcgcgctggg cgcggggcccg tgggacgcgc tgttcggcaa gggcaacatc    1380
ccggcgttcg gcgtggcgtc ggggttcgcc ctcatcggcg gcgtcgtggg cgtgttcctg    1440
ctgcccaaga tctccaagcg ccagttccgc gccgtcagcg cggcggcca ctgatcgcgg    1500 ccgccgcgcc ggagcacggc acggcggcac agcccagccg tgctagagct gtatgttttg    1560
aaagttgaaa cagaataaga agcgggcgaa acgagaaaac catgcatgtc atgtgtgtgc    1620
ttttgttgtg tgtggggtgg ggcaagcgag gcgaggtgtg tggaggtgaa gtgaaggtga    1680
gcatatccag caccagctgg taccaaggtc gggtctctgt gctagtgcta ttagctagtg    1740
taaggagcga gtaggtcagt taaggctggt gcgtcgtgag ggctgtcttg tgtgtagcta    1800
```

-continued

```
cagcagacgg ttcatcagaa ggattattcg tgcagtatat acagtacaac tagacaatga    1860
tgttgatgat tggtctagag ctagaggcct atagccctat actactgtgt attgtccgcc    1920
gttttagttt tttggtccca tcccatcaat gcaaccgcct tgttttaaaa aaaaaaa      1977
```

<210> SEQ ID NO 6
<211> LENGTH: 497
<212> TYPE: PRT
<213> ORGANISM: Zea mays

<400> SEQUENCE: 6

```
Ala Ala Asp His Val Ala Pro Ile Ser Leu Gly Arg Leu Ile Leu Ala
 1               5                  10                  15

Gly Met Val Ala Gly Val Gln Tyr Gly Trp Ala Leu Gln Leu Ser
            20                  25                  30

Leu Leu Thr Pro Tyr Val Gln Thr Leu Gly Leu Ser His Ala Leu Thr
        35                  40                  45

Ser Phe Met Trp Leu Cys Gly Pro Ile Ala Gly Leu Val Val Gln Pro
    50                  55                  60

Leu Val Gly Leu Tyr Ser Asp Arg Cys Thr Ala Arg Trp Gly Arg Arg
65                  70                  75                  80

Arg Pro Phe Ile Leu Ile Gly Cys Met Leu Ile Cys Leu Ala Val Ile
                85                  90                  95

Val Val Gly Phe Ser Ser Asp Ile Gly Ala Ala Leu Gly Asp Thr Lys
            100                 105                 110

Glu His Cys Ser Leu Tyr His Gly Pro Arg Trp His Ala Ala Ile Val
        115                 120                 125

Tyr Val Leu Gly Phe Trp Leu Leu Asp Phe Ser Asn Asn Thr Val Gln
    130                 135                 140

Gly Pro Ala Arg Ala Met Met Ala Asp Leu Cys Gly His His Gly Pro
145                 150                 155                 160

Ser Ala Ala Asn Ser Ile Phe Cys Ser Trp Met Ala Leu Gly Asn Ile
                165                 170                 175

Leu Gly Tyr Ser Ser Gly Ser Thr Asn Asn Trp His Lys Trp Phe Pro
            180                 185                 190

Phe Leu Met Thr Asn Ala Cys Cys Glu Ala Cys Ala Asn Leu Lys Gly
        195                 200                 205

Ala Phe Leu Val Ala Val Phe Leu Ile Met Cys Leu Thr Ile Thr
    210                 215                 220

Leu Phe Phe Ala Lys Glu Val Pro Tyr Arg Gly Asn Gln Asn Leu Pro
225                 230                 235                 240

Thr Lys Ala Asn Gly Glu Val Glu Thr Glu Pro Ser Gly Pro Leu Ala
                245                 250                 255

Val Leu Lys Gly Phe Lys Asn Leu Pro Thr Gly Met Pro Ser Val Leu
            260                 265                 270

Leu Val Thr Gly Leu Thr Trp Leu Ser Trp Phe Pro Phe Ile Leu Tyr
        275                 280                 285

Asp Thr Asp Trp Met Gly Arg Glu Ile Tyr His Gly Asp Pro Lys Gly
    290                 295                 300

Ser Asn Ala Gln Ile Ser Ala Phe Asp Glu Gly Val Arg Val Gly Ser
305                 310                 315                 320

Phe Gly Leu Leu Leu Asn Ser Ile Val Leu Gly Phe Ser Ser Phe Leu
                325                 330                 335

Ile Glu Pro Met Cys Arg Lys Val Gly Pro Arg Val Val Trp Val Thr
            340                 345                 350
```

```
Ser Asn Phe Met Val Cys Val Ala Met Ala Ala Thr Ala Leu Ile Ser
        355                 360                 365
Phe Trp Ser Leu Lys Asp Tyr His Gly Tyr Val Gln Asp Ala Ile Thr
        370                 375                 380
Ala Ser Thr Ser Ile Lys Ala Val Cys Leu Val Leu Phe Ala Phe Leu
385                 390                 395                 400
Gly Val Pro Leu Ala Ile Leu Tyr Ser Val Pro Phe Ala Val Thr Ala
                405                 410                 415
Gln Leu Ala Ala Thr Lys Gly Gly Gln Gly Leu Cys Thr Gly Val
                420                 425                 430
Leu Asn Ile Ser Ile Val Ile Pro Gln Val Ile Ala Leu Gly Ala
        435                 440                 445
Gly Pro Trp Asp Ala Leu Phe Gly Lys Gly Asn Ile Pro Ala Phe Gly
        450                 455                 460
Val Ala Ser Gly Phe Ala Leu Ile Gly Gly Val Val Gly Val Phe Leu
465                 470                 475                 480
Leu Pro Lys Ile Ser Lys Arg Gln Phe Arg Ala Val Ser Ala Gly Gly
                485                 490                 495
His
```

<210> SEQ ID NO 7
<211> LENGTH: 1653
<212> TYPE: DNA
<213> ORGANISM: Oryza sativa

<400> SEQUENCE: 7

```
gcacgagatc actgcttcca tcgctgccgc agttctcacc gtcggattct ccgccgacct      60
cggccgaatc ttcggcgatt ccatcacccc gggctccacc cgcctcggcg ccatcatcgt     120
ctacctcgtc ggcttctggc tcctcgacgt cggcaacaac gctacacagg acccctgcag     180
ggccttcctc gccgacctca ccgagaatga cccaaggagg actcggatag ctaatgctta     240
cttctcattg ttcatggccc tgggaaacat acttggatat gccactggag catacagtgg     300
ctggtacaag atattcccgt tcaccgttac tccatcatgt agcatcagct gtgccaactt     360
caagtctgcc tttctacttg atattatcat tttggtggtc actacatgca tcactgtagc     420
atcagtgcaa gagcctcaat cctttggaag tgatgaagca gatcacccta gcacagaaca     480
ggaagctttc ctctgggaac tttttggatc attccggtac tttacattac cggtttggat     540
ggttttgatt gttactgccc tcacatggat tggatggttt ccatttatcc tctttgatac     600
cgattggatg ggtcgagaga tctatcgtgg aagtccagat gatccaagta taactcagag     660
ctatcatgat ggtgtgagaa tgggttcttt tggtctgatg ctgaactcgg tccttcttgg     720
attcacttct attgtactag agaagttatg tcggaagtgg ggagctggac tggtgtgggg     780
tgtctccaat atcctaatgg cattgtgctt tgtggcaatg cttgtaataa catatgtggc     840
aaagaatatg gattatccac ctagtggagt accaccaacc ggcattgtca ttgcttccct     900
ggtagttttt acaattttag gagcgcccct ggcgatcacg tacagtatac catatgcaat     960
ggctgctagt cgggttgaaa atctgggact tggccaaggt ctagcaatgg cattcttaa     1020
tttggctatt gtcataccac aggttattgt gtcactgggt agcgggccct gggaccaact    1080
gtttggtggt ggcaatgcac cagcctttgc agtggctgct gctgcatctt ttatcggtgg    1140
gctggtggct attctgggcc ttccacgagc ccgcattgca tcaaggagga gaggtcaccg    1200
ataagaatat tgctacatat aaattgtcgg ccattctttg caattcgact cataagaggc    1260
```

-continued

```
actcggaacg ctatgcagtg catgggggaa ttgtatatta tctccgaatc aagaagggga   1320
taatgcttgc tttctccatg agctattttt gccttttca tgccggatca tcatatgctg    1380
tcgtacattg gatgatctta tgctgttgta cattggatgt tggtcatttg tagagatact   1440
agtgaataaa agttgcagga gttggttcac tcgagaaaat tctggtcagt atgtcgtcca   1500
tctgctgcac gacagcagtt aggagccgaa tagcatgtcc atgggttttc atcaaatgtt   1560
gtatcatcat ttgttttttg atacgttcag acggcttcag tgctgtgtga atatatatgt   1620
atggaatata tcgagaaaaa aaaaaaaaaa aaa                                1653
```

<210> SEQ ID NO 8
<211> LENGTH: 400
<212> TYPE: PRT
<213> ORGANISM: Oryza sativa

<400> SEQUENCE: 8

```
His Glu Ile Thr Ala Ser Ile Ala Ala Val Leu Thr Val Gly Phe
  1               5                  10                  15

Ser Ala Asp Leu Gly Arg Ile Phe Gly Asp Ser Ile Thr Pro Gly Ser
                 20                  25                  30

Thr Arg Leu Gly Ala Ile Ile Val Tyr Leu Val Gly Phe Trp Leu Leu
             35                  40                  45

Asp Val Gly Asn Asn Ala Thr Gln Gly Pro Cys Arg Ala Phe Leu Ala
     50                  55                  60

Asp Leu Thr Glu Asn Asp Pro Arg Arg Thr Arg Ile Ala Asn Ala Tyr
 65                  70                  75                  80

Phe Ser Leu Phe Met Ala Leu Gly Asn Ile Leu Gly Tyr Ala Thr Gly
                 85                  90                  95

Ala Tyr Ser Gly Trp Tyr Lys Ile Phe Pro Phe Thr Val Thr Pro Ser
            100                 105                 110

Cys Ser Ile Ser Cys Ala Asn Phe Lys Ser Ala Phe Leu Leu Asp Ile
            115                 120                 125

Ile Ile Leu Val Val Thr Thr Cys Ile Thr Val Ala Ser Val Gln Glu
        130                 135                 140

Pro Gln Ser Phe Gly Ser Asp Glu Ala Asp His Pro Ser Thr Glu Gln
145                 150                 155                 160

Glu Ala Phe Leu Trp Glu Leu Phe Gly Ser Phe Arg Tyr Phe Thr Leu
                165                 170                 175

Pro Val Trp Met Val Leu Ile Val Thr Ala Leu Thr Trp Ile Gly Trp
            180                 185                 190

Phe Pro Phe Ile Leu Phe Asp Thr Asp Trp Met Gly Arg Glu Ile Tyr
        195                 200                 205

Arg Gly Ser Pro Asp Asp Pro Ser Ile Thr Gln Ser Tyr His Asp Gly
    210                 215                 220

Val Arg Met Gly Ser Phe Gly Leu Met Leu Asn Ser Val Leu Leu Gly
225                 230                 235                 240

Phe Thr Ser Ile Val Leu Glu Lys Leu Cys Arg Lys Trp Gly Ala Gly
                245                 250                 255

Leu Val Trp Gly Val Ser Asn Ile Leu Met Ala Leu Cys Phe Val Ala
            260                 265                 270

Met Leu Val Ile Thr Tyr Val Ala Lys Asn Met Asp Tyr Pro Pro Ser
        275                 280                 285

Gly Val Pro Pro Thr Gly Ile Val Ile Ala Ser Leu Val Val Phe Thr
    290                 295                 300
```

```
Ile Leu Gly Ala Pro Leu Ala Ile Thr Tyr Ser Ile Pro Tyr Ala Met
305                 310                 315                 320

Ala Ala Ser Arg Val Glu Asn Leu Gly Leu Gly Gln Gly Leu Ala Met
            325                 330                 335

Gly Ile Leu Asn Leu Ala Ile Val Ile Pro Gln Val Ile Val Ser Leu
        340                 345                 350

Gly Ser Gly Pro Trp Asp Gln Leu Phe Gly Gly Asn Ala Pro Ala
            355                 360                 365

Phe Ala Val Ala Ala Ala Ser Phe Ile Gly Gly Leu Val Ala Ile
    370                 375                 380

Leu Gly Leu Pro Arg Ala Arg Ile Ala Ser Arg Arg Gly His Arg
385                 390                 395                 400

<210> SEQ ID NO 9
<211> LENGTH: 2375
<212> TYPE: DNA
<213> ORGANISM: Oryza sativa

<400> SEQUENCE: 9
gcacgaggtt ctaacccgcg ccttcgccga gggaggccga ccaacgcatc aatcaaacac      60
acaagcacac cacgcggacg cagcagcagg ggaggagaca atttcctatt cttcctcgcc     120
ccgcgtcgcc tcgcctgagt ctgactctcc aaacgccgac cagtgacgcc gcgagccttg     180
ccccttgccc gcgcagatct caccaaaccc taccagatct gcgccccgcc atggactccg     240
ccgccggcgg tggcggcctc acggccatcg gcctgcccta ccgccacctc cgcgacgccg     300
agatggagct cgtcagcctc aacggcggca ccccccgcgg aggctccccc aaggaccccg     360
acgccacgca ccagcagggg ccccccgccg cccgtaccac caccaccagg aagctcgtcc     420
tcgcctgcat ggtcgccgcc ggcgtgcagt tcggctgggc gcttcagctc tcgctcctca     480
cgccctacat ccagacccta ggaatagacc atgccatggc atcattcatt tggctttgtg     540
gacctattac tggttttgtg gttcaaccat gtgttggtgt ctggagtgac aaatgccgtt     600
caaagtatgg aagaaggaga ccgttcattt tggctggatg cttgatgata tgctttgctg     660
taactttaat cggatttttct gcagaccttg gttacatttt aggagatacc actgagcact     720
gcagtacata taaaggttca agatttcgag cagctattat tttcgttctt gggttctgga     780
tgttggatct cgcaaacaat acagttcaag gtcctgctcg tgccctttta gctgaccttt     840
caggtcctga tcagtgtaat tctgcaaatg caattttttg cacatggatg ctgttggaa      900 acgttcttgg ttttcatct ggtgctagtg ggaattggca caagtggttt cctttctaa      960 tgacaagagc atgctgtgaa gcttgtagta atttgaaagc cgcttttctg gttgcagttg    1020
tattcctttt gttttgtatg tctgttaccc tgtactttgc tgaagagatc ccgctggaac    1080
caacagatgc acaacgatta tctgattctg cgcctctcct gaatggttct agagatgata    1140
acaatgcatc aaatgaacct cgtaatggag cacttcctaa tggtcataca gatggaagca    1200
atgtcccagc taactccaac gctgaggact ccaattcaaa cagagagaat gtcgaagttt    1260
tcaatgatgg accaggagca gttttggtga atattttgac tagcatgagg catctacctc    1320
ctggaatgta ctctgttctt ctagttatgg ctctaacatg gtgtcgtgg tttcccttt     1380 tccttttga tactgactgg atgggacgtg aggtttacca tggggaccca atggcaact      1440 tgagtgaaag gaaagcttat gacaacggtg tccgagaagg tgcatttggt ttgctattga    1500
attcagttgt ccttggaatt gggtccttcc ttgttgatcc actatgccga ctgatgggtg    1560
```

-continued

```
ctagactggt ttgggcaatc agcaacttca cagtgtttat ctgcatgctg gctacagcaa    1620
tattaagttg gatctctttt gatttgtact caagtaaact tcaccacatc attggagcaa    1680
ataaaacagt gaagaattca gccttgattg ttttctccct acttggactg ccactctcga    1740
tcacatatag cgttcctttt tctgtgactg ctgagctgac tgctggaaca ggaggtggac    1800
aaggtctggc aacaggagtc ctgaaccttg caatcgttgt tccgcagata gtagtgtcac    1860
taggagcagg tccatgggat gctctctttg ggggagggaa cgtccctgct ttcgccttgg    1920
cttccgtttt ctcactagga gctggtgtcc tcgcggtcct taagctaccc aagctgccaa    1980
actcttacag atctgctggg ttccatggat ttggctgagc agaacaccag ccgcatggtg    2040
tgtaacattg agaaatgcaa ctccattttg ccattcgttt acagtgaaat gattcttttt    2100
acctactact acaacagaat aagctgaaaa gatagagatt aggatagaga gctaggtaac    2160
tagtccagtt aggttgatgt gcatacaagg caattggaag gtgtaagagc tgtatctact    2220
tttttgacag aaaaatgtaa gctctgcccg aatgacatgg cggatagatt ttacaatgga    2280
tgtaatcatg tactatatat aacacgtttt ggtcacagct tgccaagttt catgtatagt    2340
actgctacta aaaaaaaaaa aaaaaaaaaa aaaaa                               2375
```

<210> SEQ ID NO 10
<211> LENGTH: 667
<212> TYPE: PRT
<213> ORGANISM: Oryza sativa

<400> SEQUENCE: 10

```
Pro Ala Pro Ser Pro Arg Glu Ala Asp Gln Arg Ile Asn Gln Thr His
  1               5                  10                  15

Lys His Thr Thr Arg Thr Gln Gln Gln Gly Arg Arg Gln Phe Pro Ile
                 20                  25                  30

Leu Pro Arg Pro Ala Ser Pro Arg Leu Ser Leu Thr Leu Gln Thr Pro
             35                  40                  45

Thr Ser Asp Ala Ala Ser Leu Ala Pro Cys Pro Arg Arg Ser His Gln
         50                  55                  60

Thr Leu Pro Asp Leu Arg Pro Ala Met Asp Ser Ala Ala Gly Gly Gly
     65                  70                  75                  80

Gly Leu Thr Ala Ile Arg Leu Pro Tyr Arg His Leu Arg Asp Ala Glu
                 85                  90                  95

Met Glu Leu Val Ser Leu Asn Gly Gly Thr Pro Arg Gly Gly Ser Pro
                100                 105                 110

Lys Asp Pro Asp Ala Thr His Gln Gln Gly Pro Pro Ala Ala Arg Thr
            115                 120                 125

Thr Thr Thr Arg Lys Leu Val Leu Ala Cys Met Val Ala Ala Gly Val
        130                 135                 140

Gln Phe Gly Trp Ala Leu Gln Leu Ser Leu Leu Thr Pro Tyr Ile Gln
145                 150                 155                 160

Thr Leu Gly Ile Asp His Ala Met Ala Ser Phe Ile Trp Leu Cys Gly
                165                 170                 175

Pro Ile Thr Gly Phe Val Val Gln Pro Cys Val Gly Val Trp Ser Asp
            180                 185                 190

Lys Cys Arg Ser Lys Tyr Gly Arg Arg Arg Pro Phe Ile Leu Ala Gly
        195                 200                 205

Cys Leu Met Ile Cys Phe Ala Val Thr Leu Ile Gly Phe Ser Ala Asp
    210                 215                 220

Leu Gly Tyr Ile Leu Gly Asp Thr Thr Glu His Cys Ser Thr Tyr Lys
```

```
                225                 230                 235                 240
Gly Ser Arg Phe Arg Ala Ala Ile Ile Phe Val Leu Gly Phe Trp Met
                245                 250                 255
Leu Asp Leu Ala Asn Asn Thr Val Gln Gly Pro Ala Arg Ala Leu Leu
                260                 265                 270
Ala Asp Leu Ser Gly Pro Asp Gln Cys Asn Ser Ala Asn Ala Ile Phe
                275                 280                 285
Cys Thr Trp Met Ala Val Gly Asn Val Leu Gly Phe Ser Ser Gly Ala
                290                 295                 300
Ser Gly Asn Trp His Lys Trp Phe Pro Phe Leu Met Thr Arg Ala Cys
305                 310                 315                 320
Cys Glu Ala Cys Ser Asn Leu Lys Ala Ala Phe Leu Val Ala Val Val
                325                 330                 335
Phe Leu Leu Phe Cys Met Ser Val Thr Leu Tyr Phe Ala Glu Glu Ile
                340                 345                 350
Pro Leu Glu Pro Thr Asp Ala Gln Arg Leu Ser Asp Ser Ala Pro Leu
                355                 360                 365
Leu Asn Gly Ser Arg Asp Asp Asn Asn Ala Ser Asn Glu Pro Arg Asn
                370                 375                 380
Gly Ala Leu Pro Asn Gly His Thr Asp Gly Ser Asn Val Pro Ala Asn
385                 390                 395                 400
Ser Asn Ala Glu Asp Ser Asn Ser Asn Arg Glu Asn Val Glu Val Phe
                405                 410                 415
Asn Asp Gly Pro Gly Ala Val Leu Val Asn Ile Leu Thr Ser Met Arg
                420                 425                 430
His Leu Pro Pro Gly Met Tyr Ser Val Leu Leu Val Met Ala Leu Thr
                435                 440                 445
Trp Leu Ser Trp Phe Pro Phe Phe Leu Phe Asp Thr Asp Trp Met Gly
                450                 455                 460
Arg Glu Val Tyr His Gly Asp Pro Asn Gly Asn Leu Ser Glu Arg Lys
465                 470                 475                 480
Ala Tyr Asp Asn Gly Val Arg Glu Gly Ala Phe Gly Leu Leu Leu Asn
                485                 490                 495
Ser Val Val Leu Gly Ile Gly Ser Phe Leu Val Asp Pro Leu Cys Arg
                500                 505                 510
Leu Met Gly Ala Arg Leu Val Trp Ala Ile Ser Asn Phe Thr Val Phe
                515                 520                 525
Ile Cys Met Leu Ala Thr Ala Ile Leu Ser Trp Ile Ser Phe Asp Leu
                530                 535                 540
Tyr Ser Ser Lys Leu His His Ile Ile Gly Ala Asn Lys Thr Val Lys
545                 550                 555                 560
Asn Ser Ala Leu Ile Val Phe Ser Leu Leu Gly Leu Pro Leu Ser Ile
                565                 570                 575
Thr Tyr Ser Val Pro Phe Ser Val Thr Ala Glu Leu Thr Ala Gly Thr
                580                 585                 590
Gly Gly Gly Gln Gly Leu Ala Thr Gly Val Leu Asn Leu Ala Ile Val
                595                 600                 605
Val Pro Gln Ile Val Val Ser Leu Gly Ala Gly Pro Trp Asp Ala Leu
                610                 615                 620
Phe Gly Gly Gly Asn Val Pro Ala Phe Ala Leu Ala Ser Val Phe Ser
625                 630                 635                 640
Leu Gly Ala Gly Val Leu Ala Val Leu Lys Leu Pro Lys Leu Pro Asn
                645                 650                 655
```

Ser Tyr Arg Ser Ala Gly Phe His Gly Phe Gly
                660                 665

<210> SEQ ID NO 11
<211> LENGTH: 1885
<212> TYPE: DNA
<213> ORGANISM: Glycine max

<400> SEQUENCE: 11

| | | | | |
|---|---|---|---|---|
| gcacgaggag | agaaagagaa | aacatttaaa | aaaatataaa | aaaaaataaa | cctctttctc | 60 |
| tctctgaatt | tctaagcctc | tctcaaaata | atggaggagc | acaaccagg | acccagcccg | 120 |
| ttacgcaaaa | tgattttggt | gtcgtcaatg | gcggccggta | tccaattcgg | gtgggcccta | 180 |
| cagctctccc | ttctcacccc | atatgttcaa | accctaggcg | tcccgcatgc | ttgggcctca | 240 |
| tttatttggc | tatgtggccc | gatatctggg | ctgctggtgc | agcccattgt | gggctacagc | 300 |
| agcgaccgat | gccaatcccg | tttcggtcgt | cgccgtccct | ttatcctagc | cgggtctttg | 360 |
| gccgtcgcca | ttgctgtgtt | cctaattggt | tacgcggccg | atataggaca | cgcggcaggc | 420 |
| gacaacctga | cccaaaagac | tcggccacgt | gcagtggcga | tcttcgtgat | cgggttttgg | 480 |
| atcctcgacg | tggctaacaa | catgctccag | gtccatgcc | gtgcctttct | gggcgacctc | 540 |
| gctgccggga | tgagaaaaa | gacaaaggca | gccaatgcct | tcttctcttt | cttcatggcc | 600 |
| gtcggcaaca | tcctgggcta | tgctgcggga | tcctacgacg | gcctccaccg | cctcttcccc | 660 |
| ttcacggaaa | ccgaggcatg | caacgtcttc | tgcgcaaacc | tcaagagttg | cttcttcttc | 720 |
| gctatcgtcc | tcctggtggt | cctcaccacc | ttggtgctga | ttaccgtgaa | agaaactccc | 780 |
| tacacgccaa | aggcagagaa | ggaaaccgaa | gatgcagaga | agacacactt | ctcgtgcttc | 840 |
| tgcggagaac | tttgtcttgc | attcaagggg | ctgaagaggc | caatgtggat | gttgatgttg | 900 |
| gtgaccgccg | tgaactggat | agcgtggttc | ccttacttct | tgttcgacac | cgattggatg | 960 |
| ggtcgtgagg | tgtacggtgg | tgacgtgggg | cagaaggcgt | acgattcggg | agttcatgca | 1020 |
| ggttctctag | gctaatgtt | gaatgcggtg | gtgttggctg | tgatgtcatt | ggcaattgaa | 1080 |
| ccgttgggc | gtgtggttgg | gggaatcaag | tggttgtggg | gaatcgttaa | catcttgttg | 1140 |
| gctatatgct | tgggaatgac | cgttctcatc | acaaagatcg | ctgagcatga | acgtcttctt | 1200 |
| aaccctgctt | tggttgggaa | cccttccctc | ggtatcaaag | ttggttccat | ggttttcttc | 1260 |
| tctgtccttg | gaatccctct | tgcgattact | ttcagtgtcc | catttgctct | agcatctata | 1320 |
| tactccagca | cttccggagc | aggccaaggt | ctatctttgg | gtgtccttaa | tattgcaatt | 1380 |
| gtcgttccac | agatgatagt | atcaaccata | agtggacctt | gggatgcctt | gttcggcggt | 1440 |
| ggaaacttgc | ctgcattcgt | gttgggtgcg | gtggccgccg | tcgtgagtgc | aatattagca | 1500 |
| gttcttctgc | tgccaactcc | aaagaaagct | gatgaggtca | gggcttctag | cctcaacatg | 1560 |
| ggaagtttgc | attagtgtgt | ctattatagg | gctttacatg | tttcactttc | aaccttgctt | 1620 |
| tgatatggga | aaaagaactt | agtctttaga | ttcgaagtgg | gtgtgtgcat | gtgtatatta | 1680 |
| ggtattagac | atgggttta | gatgcttcca | tagccacttt | atgtccaagg | acaatcatta | 1740 |
| atttgtaaac | tttggtgcga | caattatacc | gaatagaaaa | tcattaaaca | tacatctttt | 1800 |
| tatttcacac | attaaaaaaa | tatcataata | aatatatata | ttatcatatt | ataaaagaaa | 1860 |
| tatttgaaaa | aaaaaaaaaa | aaaaa | | | | 1885 |

<210> SEQ ID NO 12
<211> LENGTH: 494

```
<212> TYPE: PRT
<213> ORGANISM: Glycine max

<400> SEQUENCE: 12

Met Glu Glu Pro Gln Pro Gly Pro Ser Pro Leu Arg Lys Met Ile Leu
 1               5                  10                  15

Val Ser Ser Met Ala Ala Gly Ile Gln Phe Gly Trp Ala Leu Gln Leu
             20                  25                  30

Ser Leu Leu Thr Pro Tyr Val Gln Thr Leu Gly Val Pro His Ala Trp
         35                  40                  45

Ala Ser Phe Ile Trp Leu Cys Gly Pro Ile Ser Gly Leu Leu Val Gln
     50                  55                  60

Pro Ile Val Gly Tyr Ser Ser Asp Arg Cys Gln Ser Arg Phe Gly Arg
 65                  70                  75                  80

Arg Arg Pro Phe Ile Leu Ala Gly Ser Leu Ala Val Ala Ile Ala Val
                 85                  90                  95

Phe Leu Ile Gly Tyr Ala Ala Asp Ile Gly His Ala Ala Gly Asp Asn
            100                 105                 110

Leu Thr Gln Lys Thr Arg Pro Arg Ala Val Ala Ile Phe Val Ile Gly
        115                 120                 125

Phe Trp Ile Leu Asp Val Ala Asn Asn Met Leu Gln Gly Pro Cys Arg
    130                 135                 140

Ala Phe Leu Gly Asp Leu Ala Ala Gly Asp Glu Lys Lys Thr Lys Ala
145                 150                 155                 160

Ala Asn Ala Phe Phe Ser Phe Phe Met Ala Val Gly Asn Ile Leu Gly
                165                 170                 175

Tyr Ala Ala Gly Ser Tyr Asp Gly Leu His Arg Leu Phe Pro Phe Thr
            180                 185                 190

Glu Thr Glu Ala Cys Asn Val Phe Cys Ala Asn Leu Lys Ser Cys Phe
        195                 200                 205

Phe Phe Ala Ile Val Leu Leu Val Leu Thr Thr Leu Val Leu Ile
    210                 215                 220

Thr Val Lys Glu Thr Pro Tyr Thr Pro Lys Ala Glu Lys Glu Thr Glu
225                 230                 235                 240

Asp Ala Glu Lys Thr His Phe Ser Cys Phe Cys Gly Glu Leu Cys Leu
                245                 250                 255

Ala Phe Lys Gly Leu Lys Arg Pro Met Trp Met Leu Met Leu Val Thr
            260                 265                 270

Ala Val Asn Trp Ile Ala Trp Phe Pro Tyr Phe Leu Phe Asp Thr Asp
        275                 280                 285

Trp Met Gly Arg Glu Val Tyr Gly Gly Asp Val Gly Gln Lys Ala Tyr
    290                 295                 300

Asp Ser Gly Val His Ala Gly Ser Leu Gly Leu Met Leu Asn Ala Val
305                 310                 315                 320

Val Leu Ala Val Met Ser Leu Ala Ile Glu Pro Leu Gly Arg Val Val
                325                 330                 335

Gly Gly Ile Lys Trp Leu Trp Gly Ile Val Asn Ile Leu Leu Ala Ile
            340                 345                 350

Cys Leu Gly Met Thr Val Leu Ile Thr Lys Ile Ala Glu His Glu Arg
        355                 360                 365

Leu Leu Asn Pro Ala Leu Val Gly Asn Pro Ser Leu Gly Ile Lys Val
    370                 375                 380

Gly Ser Met Val Phe Phe Ser Val Leu Gly Ile Pro Leu Ala Ile Thr
385                 390                 395                 400
```

```
Phe Ser Val Pro Phe Ala Leu Ala Ser Ile Tyr Ser Ser Thr Ser Gly
                405                 410                 415

Ala Gly Gln Gly Leu Ser Leu Gly Val Leu Asn Ile Ala Ile Val Val
            420                 425                 430

Pro Gln Met Ile Val Ser Thr Ile Ser Gly Pro Trp Asp Ala Leu Phe
            435                 440                 445

Gly Gly Gly Asn Leu Pro Ala Phe Val Leu Gly Ala Val Ala Ala Val
        450                 455                 460

Val Ser Ala Ile Leu Ala Val Leu Leu Leu Pro Thr Pro Lys Lys Ala
465                 470                 475                 480

Asp Glu Val Arg Ala Ser Ser Leu Asn Met Gly Ser Leu His
                485                 490

<210> SEQ ID NO 13
<211> LENGTH: 1041
<212> TYPE: DNA
<213> ORGANISM: Glycine max
<220> FEATURE:
<221> NAME/KEY: unsure
<222> LOCATION: (1007)

<400> SEQUENCE: 13
gcacgagctc acactctctc tttctttctt cctgctgcta caatatggag cctctctctt      60
ccaccaaaca caacaacaat ctctccaagc cttcctccct ccacacggag ctccgccgc     120 cggaggccag tccctccgg aagatcatgg tggtggcctc catcgccgcc ggggtgcaat      180
tcgggtgggc cctacagctc tctctactta ccccttacgt ccaactgctg gggattcccc      240
acacttgggc cgccttcatc tggctctgcg gcccaatctc cggcatgctc gtccagccca      300
tcgtgggata ccacagcgac cgctgcacct cccgcttcgg ccgccgccgc cccttcatcg      360
ccgccggctc cctcgccgtc gccatcgccg tcttccttat cggctacgcc gccgacctcg      420
gccacatgtt cggcgactcc ctagccaaaa aaaccgcccc gcgccatcgc atcttcgttg      480
tcggcttctg gattctcgac gtcgcaaaca acatgctaca agggccctgc cgcgccctcc      540
tgggcgacct ctgcgccgga gaacaacgga aaacgcgaaa cgcaaacgcc ttcttctcct      600
tcttcatggc cgtcggaaac gtcctgggct acgccgcggg ctcttacagc ggcctccaca      660
acgtcttccc tttcactaaa acaaaagcat gtgatgttta ctgcgcgaat tgaagagtt      720 gtttcttcct ctccatcgcg cttcttctca ctctctccac aatcgccttg acctacgtga      780
aggagaaaac ggtgtcgtca gagaaaacgg tgaggagttc ggtggaggag gatgggtccc      840 acggggggcat gccgtgcttc gggcaattat tcggtgcgtt ccgcgaactg aagcgtccca      900
tgtggatcct tctgttggtg acgtgtctga actgggattg cctggttcct tttttgctat      960
tcgacaccga ctgggattgg ggcgtgaggt gtacggaggg aaaattnggg gaaaggaaag     1020
ggtacgataa ggggttccgt t                                               1041

<210> SEQ ID NO 14
<211> LENGTH: 322
<212> TYPE: PRT
<213> ORGANISM: Glycine max
<220> FEATURE:
<221> NAME/KEY: UNSURE
<222> LOCATION: (311)
<220> FEATURE:
<221> NAME/KEY: UNSURE
<222> LOCATION: (321)

<400> SEQUENCE: 14
```

```
Met Glu Pro Leu Ser Ser Thr Lys His Asn Asn Leu Ser Lys Pro
 1               5                  10                 15

Ser Ser Leu His Thr Glu Ala Pro Pro Glu Ala Ser Pro Leu Arg
             20                  25                 30

Lys Ile Met Val Val Ala Ser Ile Ala Ala Gly Val Gln Phe Gly Trp
                 35                  40                  45

Ala Leu Gln Leu Ser Leu Leu Thr Pro Tyr Val Gln Leu Leu Gly Ile
     50                  55                  60

Pro His Thr Trp Ala Ala Phe Ile Trp Leu Cys Gly Pro Ile Ser Gly
 65              70                  75                  80

Met Leu Val Gln Pro Ile Val Gly Tyr His Ser Asp Arg Cys Thr Ser
                 85                  90                  95

Arg Phe Gly Arg Arg Arg Pro Phe Ile Ala Ala Gly Ser Leu Ala Val
             100                 105                 110

Ala Ile Ala Val Phe Leu Ile Gly Tyr Ala Ala Asp Leu Gly His Met
         115                 120                 125

Phe Gly Asp Ser Leu Ala Lys Lys Thr Ala Pro Arg His Arg Ile Phe
130                 135                 140

Val Val Gly Phe Trp Ile Leu Asp Val Ala Asn Asn Met Leu Gln Gly
145                 150                 155                 160

Pro Cys Arg Ala Leu Leu Gly Asp Leu Cys Ala Gly Glu Gln Arg Lys
                 165                 170                 175

Thr Arg Asn Ala Asn Ala Phe Phe Ser Phe Phe Met Ala Val Gly Asn
             180                 185                 190

Val Leu Gly Tyr Ala Ala Gly Ser Tyr Ser Gly Leu His Asn Val Phe
         195                 200                 205

Pro Phe Thr Lys Thr Lys Ala Cys Asp Val Tyr Cys Ala Asn Leu Lys
210                 215                 220

Ser Cys Phe Phe Leu Ser Ile Ala Leu Leu Leu Thr Leu Ser Thr Ile
225                 230                 235                 240

Ala Leu Thr Tyr Val Lys Glu Lys Thr Val Ser Ser Glu Lys Thr Val
                 245                 250                 255

Arg Ser Ser Val Glu Glu Asp Gly Ser His Gly Gly Met Pro Cys Phe
             260                 265                 270

Gly Gln Leu Phe Gly Ala Phe Arg Glu Leu Lys Arg Pro Met Trp Ile
         275                 280                 285

Leu Leu Leu Val Thr Cys Leu Asn Trp Asp Cys Leu Val Pro Phe Leu
290                 295                 300

Leu Phe Asp Thr Asp Trp Xaa Gly Arg Glu Val Tyr Gly Gly Lys Ile
305                 310                 315                 320

Xaa Gly

<210> SEQ ID NO 15
<211> LENGTH: 578
<212> TYPE: DNA
<213> ORGANISM: Vernonia mespilifolia

<400> SEQUENCE: 15
gcacgaggtt ggcttggcgg tgtgaaacgg ttatggggtg gcatcaattt ccttctagct     60
gtttgtttgg ccatgacggt ggtggtgacc aaaatggcag actctgaacg acagtttaag    120
acgttgcccg acggtagcaa aaccgcgttg ccaccaggcg gcgacattaa agccggtgct    180
ttgtcaattt ttgccgtcct cggtgcccca ctagctgtga ctttcagtgt tccatgtgct    240
```

```
cttgcatcaa tattttctaa cagttcagga gctggacaag gtctatcact tggtgttttg      300
aatctagcaa tcgtcatacc acagatgttc gtatcagtac taagtggacc atgggacgca      360
ctgttcggcg gtggaaactt accagcattt gtggttggag caatttcggc tgcagtaagt      420
gggatattat cgttcaccat gcttccttcg ccacccccag atgtcgtact ttcaaaggtt      480
tccggaggtg ggatgcatta gagagtaaat aactgccact caacacgtcc cgattgtgtc      540
agattgggac atttaggacc aaaaaaaaaa aaaaaaaa                              578
```

<210> SEQ ID NO 16
<211> LENGTH: 166
<212> TYPE: PRT
<213> ORGANISM: Vernonia mespilifolia

<400> SEQUENCE: 16

```
Ala Arg Gly Trp Leu Gly Gly Val Lys Arg Leu Trp Gly Gly Ile Asn
  1               5                  10                  15

Phe Leu Leu Ala Val Cys Leu Ala Met Thr Val Val Thr Lys Met
             20                  25                  30

Ala Asp Ser Glu Arg Gln Phe Lys Thr Leu Pro Asp Gly Ser Lys Thr
         35                  40                  45

Ala Leu Pro Pro Gly Gly Asp Ile Lys Ala Gly Ala Leu Ser Ile Phe
     50                  55                  60

Ala Val Leu Gly Ala Pro Leu Ala Val Thr Phe Ser Val Pro Cys Ala
 65                  70                  75                  80

Leu Ala Ser Ile Phe Ser Asn Ser Ser Gly Ala Gly Gln Gly Leu Ser
                 85                  90                  95

Leu Gly Val Leu Asn Leu Ala Ile Val Ile Pro Gln Met Phe Val Ser
            100                 105                 110

Val Leu Ser Gly Pro Trp Asp Ala Leu Phe Gly Gly Asn Leu Pro
        115                 120                 125

Ala Phe Val Val Gly Ala Ile Ser Ala Ala Val Ser Gly Ile Leu Ser
    130                 135                 140

Phe Thr Met Leu Pro Ser Pro Pro Asp Val Val Leu Ser Lys Val
145                 150                 155                 160

Ser Gly Gly Gly Met His
                165
```

<210> SEQ ID NO 17
<211> LENGTH: 1062
<212> TYPE: DNA
<213> ORGANISM: Triticum aestivum

<400> SEQUENCE: 17

```
ctggaatgcc gtcagtgctc ctcgtcaccg gcctcacctg gctgtcctgg ttccccttca       60
tcctgtacga caccgactgg atgggtcgtg agatctacca cggtgacccc aagggaaccc      120
ccgacgaggc caacgcgttc caggcaggtg tcagggccgg ggcgttcggc ctgctactca      180
actcggtcgt cctggggttc agctcgttcc tgatcgagcc gctgtgcaag aggctaggcc      240
cgcgggtggt gtgggtgtca agcaacttcc tcgtctgcat ctccatggcc gccatttgca      300
tcataagctg gtgggccact caggacctgc atgggtacat ccagcacgcc atcaccgcca      360
gcaaggagat caagatcgtc tccctcgccc tcttcgcctt cctcggaatc cctctcgcca      420
ttctgtacag tgtcccttc gcggtgacgg cgcagctggc ggcgaacaga ggcggtggcc      480
aagggctgtg cacgggcgtg ctgaacatcg ccatcgtgat accccaggtg atcatcgcgg      540
```

```
tgggggcggg gccgtgggac gagctgttcg gcaagggcaa catcccggcg ttcggcgtgg    600
cgtccgcctt cgcgctcatc ggcggcatcg tcggcatatt cctgctgccc aagatctcca    660
ggcgccagtt ccgggccgtc agcgcggcg gtcactgacc gcgccgcgcg ccggtcggcc    720
tgagcatggc gaaggccgat cgcgccggcc cgaaggtccc agcccagctc ggcatttacc    780
aaattttcgc ataggcgtaa ctaggggct ctcgcctaag gactccgtag agcagaataa    840
gaattgtgag gaacctgtat gtgttgtgtc tgtatgtgcg tgtaagtcag tgcgtgtagc    900
ggaaaatgga cagaggaatg cgggcatcca tcgccggctg gggtgtcgtc tttgggttgt    960
gacttgtgtg tagcaaacca aggtgatcaa gtgagggga aagaatggat gatgaacttt   1020
cagcgacaaa aaaaaaaaa aaaaaaaaa aaaaaaaaa aa                        1062
```

<210> SEQ ID NO 18
<211> LENGTH: 232
<212> TYPE: PRT
<213> ORGANISM: Triticum aestivum

<400> SEQUENCE: 18

```
Ala Gly Met Pro Ser Val Leu Leu Val Thr Gly Leu Thr Trp Leu Ser
 1               5                  10                  15

Trp Phe Pro Phe Ile Leu Tyr Asp Thr Asp Trp Met Gly Arg Glu Ile
                20                  25                  30

Tyr His Gly Asp Pro Lys Gly Thr Pro Asp Glu Ala Asn Ala Phe Gln
            35                  40                  45

Ala Gly Val Arg Ala Gly Ala Phe Gly Leu Leu Leu Asn Ser Val Val
        50                  55                  60

Leu Gly Phe Ser Ser Phe Leu Ile Glu Pro Leu Cys Lys Arg Leu Gly
    65                  70                  75                  80

Pro Arg Val Val Trp Val Ser Ser Asn Phe Leu Val Cys Ile Ser Met
                85                  90                  95

Ala Ala Ile Cys Ile Ile Ser Trp Trp Ala Thr Gln Asp Leu His Gly
            100                 105                 110

Tyr Ile Gln His Ala Ile Thr Ala Ser Lys Glu Ile Lys Ile Val Ser
        115                 120                 125

Leu Ala Leu Phe Ala Phe Leu Gly Ile Pro Leu Ala Ile Leu Tyr Ser
    130                 135                 140

Val Pro Phe Ala Val Thr Ala Gln Leu Ala Ala Asn Arg Gly Gly Gly
145                 150                 155                 160

Gln Gly Leu Cys Thr Gly Val Leu Asn Ile Ala Ile Val Ile Pro Gln
                165                 170                 175

Val Ile Ala Val Gly Ala Gly Pro Trp Asp Glu Leu Phe Gly Lys
            180                 185                 190

Gly Asn Ile Pro Ala Phe Gly Val Ala Ser Ala Phe Ala Leu Ile Gly
        195                 200                 205

Gly Ile Val Gly Ile Phe Leu Leu Pro Lys Ile Ser Arg Arg Gln Phe
    210                 215                 220

Arg Ala Val Ser Gly Gly Gly His
225                 230
```

<210> SEQ ID NO 19
<211> LENGTH: 2083
<212> TYPE: DNA
<213> ORGANISM: Triticum aestivum
<220> FEATURE:
<221> NAME/KEY: UNSURE
<222> LOCATION: (1093)

<400> SEQUENCE: 19

```
gcacgagcac accacaccac acctctctct ctctcactcg cactttccgc tctcgtctcc      60
tcctcttcct cctcccgtca gacccttctt ccccggcgtt gatccgatca acgtcctcct     120
ccgtcctgcc cctagatcct tggccgggca gggatacgcc gtagaattga taggcgaacg     180
gacgaggtgg tgatcgccag gcggcctct ctgccatggc gcgcggcgga ggcaacggcg      240
aggtggagct ctcggtcggg gtcggcggcg gaggcggcgg cgccgccggc gggggggagc     300
aacccgccgt ggacatcagc ctcggcagac tcatcctcgc cggcatggtc gccggcggcg     360
tgcagtacgg atgggcgctc cagctctccc tgctcacccc ctacgtccag actctgggac     420
tttcgcatgc tctgacttca ttcatgtggc tctgcggccc tattgctgga ttagtggttc     480
aaccatgcgt tgggctctac agtgacaagt gcacatctag atggggaaga cgcagaccgt     540
ttattctgac aggatgcatc ctcatctgca ttgctgttgt ggtcgtcggc ttctcggctg     600
acattggagc tggtctgggt gacagcaagg aagagtgcag tctctatcat gggcctcgtt     660
ggcacgctgc aattgtgtat gttcttggat tctggctcct tgacttctcc aacaacactg     720
tgcaaggtcc agcgcgtgct ctgatggctg atttatcagc tcagcatgga cccagtgcag     780
caaattcaat cttctgttct tggatggcgc taggaaatat ccttggatac tcctctggtt     840
ccacaaacaa ctggcacaag tggtttccgt tcctccggac aagggcttgc tgtgaagcct     900
gcgcaaatct gaaaggcgca tttctggtgg cagtgctggt cctggccttc tgtttggtga     960
taactgtgat cttcgccaag gagataccgt acaaggcgat tgcgcccctc ccaacaaagg    1020
gcaatggcca ggttgaagtc gagcccaccg ggccgctcgc cgtgttcaaa ggcttcaaga    1080
acttgcctcc tgnaatgccg tcggtgctcc tcgtcactgg cctcacctgg ctgtcctggt    1140
tccccttcat cctgtacgac accgactgga tgggtcgtga gatctaccac ggtgacccca    1200
agggaacccc cgacgaggcc aacgcgttcc aggcaggtgt cagggccggg gcgttcggcc    1260
tgctactcaa ctcggtcgtc ctggggttca gctcgttcct gatcgagccg ctgtgcaaga    1320
ggctaggccc gcgggtggtg tgggtgtcga gcaacttcct cgtctgcctc tccatggccg    1380
cgatttgcat cataagctgg tgggctactc aggacttgca tgggtatatc cagcacgcca    1440
tcaccgccag caaggagatc aagatcgtct ccctcgccct cttcgccttc ctcggaatcc    1500
ctctcgccat tctgtacagt gtccctttcg cggtgacggc gcagctggcg gcgaagagag    1560
gcggtggcca agggctgtgc acgggcgtgc tcaacatcgc catcgtgata ccccaggtga    1620
tcatcgcggt gggggcgggg ccgtgggacg agctgttcgg caagggcaac atcccggcgt    1680
tcggcatggc ctccgccttc gcgctcatcg gcggcatcgt cggcatattc ctgctgccca    1740
agatctccag gcgccagttc cgggccgtca gcggcggcgg tcactgagca tggccaaggc    1800
cggaggtccc agcccagccc gccatttacc aaattttcgc ataggcgtaa ctaggtggct    1860
ctcgcctaag gactccgtag agcagaataa gaattgtgag gaacctgtat gtgttgtgtc    1920
tgtatgtgcg tgtaagtcag tgcgtgtagc ggaaaatgga cagaggaatg tgggcatcca    1980
tcaccggctg gggtgtcgtc tttgggttgt gacttgtgtg tagcaaacca aggtgatcaa    2040
gtgaggggaa atgaatggat gatgaacttt cagcgacaaa aaa                      2083
```

<210> SEQ ID NO 20
<211> LENGTH: 522
<212> TYPE: PRT
<213> ORGANISM: Triticum aestivum

<400> SEQUENCE: 20

```
Met Ala Arg Gly Gly Asn Gly Glu Val Glu Leu Ser Val Gly Val
  1               5                  10                  15

Gly Gly Gly Gly Gly Ala Gly Gly Glu Gln Pro Ala Val
                 20                  25                  30

Asp Ile Ser Leu Gly Arg Leu Ile Leu Ala Gly Met Val Ala Gly
                 35                  40                  45

Val Gln Tyr Gly Trp Ala Leu Gln Leu Ser Leu Leu Thr Pro Tyr Val
         50                  55                  60

Gln Thr Leu Gly Leu Ser His Ala Leu Thr Ser Phe Met Trp Leu Cys
 65                  70                  75                  80

Gly Pro Ile Ala Gly Leu Val Val Gln Pro Cys Val Gly Leu Tyr Ser
                 85                  90                  95

Asp Lys Cys Thr Ser Arg Trp Gly Arg Arg Pro Phe Ile Leu Thr
                100                 105                 110

Gly Cys Ile Leu Ile Cys Ile Ala Val Val Val Gly Phe Ser Ala
                115                 120                 125

Asp Ile Gly Ala Gly Leu Gly Asp Ser Lys Glu Glu Cys Ser Leu Tyr
        130                 135                 140

His Gly Pro Arg Trp His Ala Ile Val Tyr Val Leu Gly Phe Trp
145                 150                 155                 160

Leu Leu Asp Phe Ser Asn Asn Thr Val Gln Gly Pro Ala Arg Ala Leu
                165                 170                 175

Met Ala Asp Leu Ser Ala Gln His Gly Pro Ser Ala Ala Asn Ser Ile
                180                 185                 190

Phe Cys Ser Trp Met Ala Leu Gly Asn Ile Leu Gly Tyr Ser Ser Gly
                195                 200                 205

Ser Thr Asn Asn Trp His Lys Trp Phe Pro Phe Leu Arg Thr Arg Ala
        210                 215                 220

Cys Cys Glu Ala Cys Ala Asn Leu Lys Gly Ala Phe Leu Val Ala Val
225                 230                 235                 240

Leu Val Leu Ala Phe Cys Leu Val Ile Thr Val Ile Phe Ala Lys Glu
                245                 250                 255

Ile Pro Tyr Lys Ala Ile Ala Pro Leu Pro Thr Lys Gly Asn Gly Gln
                260                 265                 270

Val Glu Val Glu Pro Thr Gly Pro Leu Ala Val Phe Lys Gly Phe Lys
        275                 280                 285

Asn Leu Pro Pro Met Pro Ser Val Leu Leu Val Thr Gly Leu Thr Trp
        290                 295                 300

Leu Ser Trp Phe Pro Phe Ile Leu Tyr Asp Thr Asp Trp Met Gly Arg
305                 310                 315                 320

Glu Ile Tyr His Gly Asp Pro Lys Gly Thr Pro Asp Glu Ala Asn Ala
                325                 330                 335

Phe Gln Ala Gly Val Arg Ala Gly Ala Phe Gly Leu Leu Asn Ser
                340                 345                 350

Val Val Leu Gly Phe Ser Ser Phe Leu Ile Glu Pro Leu Cys Lys Arg
                355                 360                 365

Leu Gly Pro Arg Val Val Trp Val Ser Ser Asn Phe Leu Val Cys Leu
        370                 375                 380

Ser Met Ala Ala Ile Cys Ile Ile Ser Trp Trp Ala Thr Gln Asp Leu
385                 390                 395                 400

His Gly Tyr Ile Gln His Ala Ile Thr Ala Ser Lys Glu Ile Lys Ile
                405                 410                 415
```

-continued

```
Val Ser Leu Ala Leu Phe Ala Phe Leu Gly Ile Pro Leu Ala Ile Leu
        420                 425                 430

Tyr Ser Val Pro Phe Ala Val Thr Ala Gln Leu Ala Ala Lys Arg Gly
        435                 440                 445

Gly Gly Gln Gly Leu Cys Thr Gly Val Leu Asn Ile Ala Ile Val Ile
        450                 455                 460

Pro Gln Val Ile Ile Ala Val Gly Ala Gly Pro Trp Asp Glu Leu Phe
465                 470                 475                 480

Gly Lys Gly Asn Ile Pro Ala Phe Gly Met Ala Ser Ala Phe Ala Leu
                485                 490                 495

Ile Gly Gly Ile Val Gly Ile Phe Leu Leu Pro Lys Ile Ser Arg Arg
        500                 505                 510

Gln Phe Arg Ala Val Ser Gly Gly Gly His
        515                 520

<210> SEQ ID NO 21
<211> LENGTH: 2160
<212> TYPE: DNA
<213> ORGANISM: Triticum aestivum

<400> SEQUENCE: 21
gcacgagacc accctctct ctctctctca ctcgcgcttt ccgctctcgt ctcctcctct     60
tcctcctccc gtcagcccct tcttcccgg cgttgatccg atcgacgtcc tccctcctcc    120
ccggcgttga tccgacgcgc cgtagagttg ataggcgaac gaacggggcg gtgatcgtcc    180
gggcggcccc cctgcgacga tggcgcgcgg cggcggcaac ggcgaggtgg agctctcggt    240
gggggtcggc ggaggcggcg ccggcgccgg cggggcggac gccccgccg tggacatcag    300 cctcggcagg ctcatcctcg ccggcatggt cgccggcggc gtgcagtacg gatgggcgct    360
ccagctctcc ctgctcaccc cctacgtcca gactctggga cttcgcatg ctctgacttc    420 attcatgtgg ctctgcggcc ctattgctgg attagtggtt caaccatgcg ttgggctcta    480
cagtgacaag tgcacttcaa gatggggaag acgcagaccg ttcattctga caggatgtat    540
cctcatctgc attgctgtcg tggtcgtcgg cttctcggct gacattggag ctgctctggg    600
tgacagcaag gaagagtgca gtctctatca tgggcctcgt tggcacgctg caattgtgta    660
tgttcttgga ttctggctcc ttgacttctc caacaacaca gtgcaaggac cagcgcgtgc    720
tctgatggct gatttatcag cccagcatgg acccagtgca gcaaattcaa tcttctgttc    780
ttggatggca ctgggaaata tcctaggata tcatctggt tccacaaata actggcacaa    840
gtggtttccg ttcctccgga caagggcttg ctgtgaagcc tgcgcaaatc tgaaaggcgc    900
atttctggtg gcagtgctgt tcctggcctt ctgtttggtg ataacgtga tcttcgccaa    960 ggagataccg tacaaggcga ttgcgccct cccaacaaag gccaatggcc aggttgaagt   1020
cgagcccacc gggccgctcg ccgtcttcaa aggcttcaag aacttgcctc tggaatgcc    1080 gtcagtgctc ctcgtcaccg gcctcacctg gctgtcctgg ttccccttca tcctgtacga   1140
caccgactgg atgggtcgtg agatctacca cggtgacccc aagggaaccc ccgacgaggc   1200
caacgcgttc caggcaggtg tcagggccgg ggcgttcggc ctgctactca actcggtcgt   1260 cctgggttc agctcgttcc tgatcgagcc gctgtgcaag aggctaggcc cgcgggtggt   1320
gtgggtgtca agcaacttcc tcgtctgcct ctccatggcc gccattgca tcataagctg   1380 gtgggccact caggacctgc atgggtacat ccagcacgcc atcaccgcca gcaaggagat   1440
caagatcgtc tccctcgccc tcttcgcctt cctcggaatc cctctcgcca ttctgtacag   1500
```

-continued

```
tgtcactttc gccgtgacgg cgcagctggc ggcgaacaga tgcggtgggc aatggctgtg    1560
cacgggcgtg ctgaacatcg ccatcgcgat accccaggtg atcatcgcgt tgggggcggg    1620
gccgtgggac gagctgttcg gcaagggcaa catcccggcg ttcggcgtgg cgtccgcctt    1680
cgcgctcatc ggcggcatcg tcggcatatt cctgctgccc aagatctcca ggctccagtt    1740
ccgggccgtc agcggcggcg gtcactgacc gcgccgcgcg ccggtcggcc tgagcatggc    1800
gaaggccgat cgcgccggcc cgaaggtccc agcccagctc ggcatttacc aaattttcgc    1860
ataggcgtaa ctaggggggct ctcgcctaag gactccgtag agcagaataa gaattgtgag    1920
gaacctgtat gtgttgtgtc tgtatgtgcg tgtaagtcag tgcgtgtagc ggaaaatgga    1980
cagaggaatg cgggcatcca tcgccggctg gggtgtcgtc tttgggttgt gacttgtgtg    2040
tagcaaacca aggtgatcaa gtgagggggaa aagaatggat gatgaacttt cagcgacaaa    2100
aaaaaaaaaa aaaaaaaaaa aaaaaataa aaaaaaaaaa aagaaaaaaa taaaaaaaaa     2160
```

<210> SEQ ID NO 22
<211> LENGTH: 522
<212> TYPE: PRT
<213> ORGANISM: Triticum aestivum

<400> SEQUENCE: 22

```
Met Ala Arg Gly Gly Gly Asn Gly Glu Val Glu Leu Ser Val Gly Val
  1               5                  10                  15

Gly Gly Gly Gly Ala Gly Ala Gly Gly Ala Asp Ala Pro Ala Val Asp
             20                  25                  30

Ile Ser Leu Gly Arg Leu Ile Leu Ala Gly Met Val Ala Gly Gly Val
         35                  40                  45

Gln Tyr Gly Trp Ala Leu Gln Leu Ser Leu Leu Thr Pro Tyr Val Gln
     50                  55                  60

Thr Leu Gly Leu Ser His Ala Leu Thr Ser Phe Met Trp Leu Cys Gly
 65                  70                  75                  80

Pro Ile Ala Gly Leu Val Val Gln Pro Cys Val Gly Leu Tyr Ser Asp
                 85                  90                  95

Lys Cys Thr Ser Arg Trp Gly Arg Arg Pro Phe Ile Leu Thr Gly
            100                 105                 110

Cys Ile Leu Ile Cys Ile Ala Val Val Val Gly Phe Ser Ala Asp
        115                 120                 125

Ile Gly Ala Ala Leu Gly Asp Ser Lys Glu Glu Cys Ser Leu Tyr His
    130                 135                 140

Gly Pro Arg Trp His Ala Ala Ile Val Tyr Val Leu Gly Phe Trp Leu
145                 150                 155                 160

Leu Asp Phe Ser Asn Asn Thr Val Gln Gly Pro Ala Arg Ala Leu Met
                165                 170                 175

Ala Asp Leu Ser Ala Gln His Gly Pro Ser Ala Asn Ser Ile Phe
            180                 185                 190

Cys Ser Trp Met Ala Leu Gly Asn Ile Leu Gly Tyr Ser Ser Gly Ser
        195                 200                 205

Thr Asn Asn Trp His Lys Trp Phe Pro Phe Leu Arg Thr Arg Ala Cys
    210                 215                 220

Cys Glu Ala Cys Ala Asn Leu Lys Gly Ala Phe Leu Val Ala Val Leu
225                 230                 235                 240

Phe Leu Ala Phe Cys Leu Val Ile Thr Val Ile Phe Ala Lys Glu Ile
                245                 250                 255
```

```
Pro Tyr Lys Ala Ile Ala Pro Leu Pro Thr Lys Ala Asn Gly Gln Val
             260                 265                 270

Glu Val Glu Pro Thr Gly Pro Leu Ala Val Phe Lys Gly Phe Lys Asn
             275                 280                 285

Leu Pro Pro Gly Met Pro Ser Val Leu Val Thr Gly Leu Thr Trp
             290                 295                 300

Leu Ser Trp Phe Pro Phe Ile Leu Tyr Asp Thr Asp Trp Met Gly Arg
305                 310                 315                 320

Glu Ile Tyr His Gly Asp Pro Lys Gly Thr Pro Asp Glu Ala Asn Ala
                 325                 330                 335

Phe Gln Ala Gly Val Arg Ala Gly Ala Phe Gly Leu Leu Leu Asn Ser
             340                 345                 350

Val Val Leu Gly Phe Ser Ser Phe Leu Ile Glu Pro Leu Cys Lys Arg
             355                 360                 365

Leu Gly Pro Arg Val Val Trp Val Ser Ser Asn Phe Leu Val Cys Leu
             370                 375                 380

Ser Met Ala Ala Ile Cys Ile Ile Ser Trp Trp Ala Thr Gln Asp Leu
385                 390                 395                 400

His Gly Tyr Ile Gln His Ala Ile Thr Ala Ser Lys Glu Ile Lys Ile
                 405                 410                 415

Val Ser Leu Ala Leu Phe Ala Phe Leu Gly Ile Pro Leu Ala Ile Leu
             420                 425                 430

Tyr Ser Val Thr Phe Ala Val Thr Ala Gln Leu Ala Ala Asn Arg Cys
             435                 440                 445

Gly Gly Gln Trp Leu Cys Thr Gly Val Leu Asn Ile Ala Ile Ala Ile
             450                 455                 460

Pro Gln Val Ile Ile Ala Leu Gly Ala Gly Pro Trp Asp Glu Leu Phe
465                 470                 475                 480

Gly Lys Gly Asn Ile Pro Ala Phe Gly Val Ala Ser Ala Phe Ala Leu
                 485                 490                 495

Ile Gly Gly Ile Val Gly Ile Phe Leu Leu Pro Lys Ile Ser Arg Leu
             500                 505                 510

Gln Phe Arg Ala Val Ser Gly Gly Gly His
             515                 520

<210> SEQ ID NO 23
<211> LENGTH: 2030
<212> TYPE: DNA
<213> ORGANISM: Triticum aestivum

<400> SEQUENCE: 23
cggaagcgac gccgcgcggc ccaaggagga acagggcagc ggcgcggggg cgggggaagg      60
cggcatgaag ggcgcgccca agtggcgggt ggtgctggcc tgcatggtcg ccgccggcgt     120
gcagttcggc tgggcgctcc agctctccct cctcaccccc tacatccaga ctctaggaat     180
agaccatgcc atggcgtcct tcatttggct ttgcgggccc attactggtt ttgtggttca     240
accgtgtgtt ggtgtctgga gtgacaagtg ccgctccaag tacgggagga acggccgtt      300
cattttggct ggatgcgtgc tgatttgtgc agctgtaact ttagtcgggt tttctgcaga     360
ccttggctac atgttaggag acaccactga gcactgcagt acatacaaag gtctacgata     420
tcgagctgct tttattttca tttttggatt ctggatgctg accttgcaa ataatacagt      480
tcaaggacct gctcgtgccc tctagctga tctttcaggt cccgatcaat gtaattcggc     540
aaatgcaata ttctgctcat ggatggctgt tggaaacgtt cttggttttt cagctggtgc     600
```

```
gagtgggaat tggcacaagt ggtttccttt tctgatgact agggcctgtt gtgaagcttg    660
tggtaatttg aaagcagctt tcttgattgc agttgtattc cttctgtttt gcatggctgt    720
taccctctac tttgctgaag agattccact ggaaccaaag gatgcacagc agttatctga    780
ctcggctcct ctactgaacg gttctagaga tgatcatgat gcttcaagtg aacagactaa    840
tggaggactt tctaacggtc atgctgatgc aaaccatgtc tcagctaact ccagtgcaga    900
tgcaggttcc aactcgaaca aggacgatgt tgaggctttc aatgatggac aggagcagt    960
tttggttaaa attttgacta gcatgaggca tctacctcct ggaatgtatt ccgtgcttct   1020
ggttatggcc ctaacatggc tgtcgtggtt tccctttttc ctttttgaca ccgactggat   1080
ggggcgtgag gtttatcacg gtgacccaaa aggaaacgcg agtgaaagga agcttatga   1140
tgatggtgtc cgagaaggtg catttggttt gctattgaat tcagtcgtcc ttgggattgg   1200
ctctttcctt atcgatccat tatgccggat gattggtgca agattggttt gggcaatcag   1260
caacttcata gtgtttgcct gcatgttggc tacaacaata ctaagttgga tctcctatga   1320
cctgtactcg agcaagcttc aacatattgt cggggcagat aaaacagtca agacctcagc   1380
gcttattctt ttctctcttc tcggattgcc actctcgatc acttatagtg ttccgttctc   1440
cgtgactgct gagctgactg ccggaacagg aggcggacaa ggtttggcta ctggagttct   1500
gaatcttgcc atcgtcgctc ctcagatagt agtgtcactc ggagcaggcc atgggacaa   1560
gctcttgggg ggagggaacg tccccgcttt cgccctggcc tcggtcttct cgctagcagc   1620
cggagtgctc gcggtgatca agctgcccaa gttgtcgaac aattaccaat ccgccggctt   1680
ccacatgggc tgaaccctaa agcccgaagc cagctgctgt gtgtaacatc cagatgttta   1740
gtaccaatcc gccggtttcc atattaagat tcgtttatat ggagatgatt cttttttctcc   1800
tcttgctaga tacacagtta ataagactac agatcagata gactaggata aagagatagt   1860
ttttaggcct gtgtgcatac aagtgtcgat gagaagttgt aaaacatgta cactgttttt   1920
ttgtactgta tatgtagtga aatttcatag atggccggat gtgttctggt ccgataaaaa   1980
aaaaaaaaaa aaaaaaaaaa aaaaaaaaaa aaaaaaaaaa aaaaaaaaaa             2030
```

<210> SEQ ID NO 24
<211> LENGTH: 563
<212> TYPE: PRT
<213> ORGANISM: Triticum aestivum

<400> SEQUENCE: 24

```
Gly Ser Asp Ala Ala Arg Pro Lys Glu Glu Gln Gly Ser Gly Ala Gly
  1               5                  10                  15

Ala Gly Glu Gly Gly Met Lys Gly Ala Pro Lys Trp Arg Val Val Leu
                 20                  25                  30

Ala Cys Met Val Ala Ala Gly Val Gln Phe Gly Trp Ala Leu Gln Leu
             35                  40                  45

Ser Leu Leu Thr Pro Tyr Ile Gln Thr Leu Gly Ile Asp His Ala Met
         50                  55                  60

Ala Ser Phe Ile Trp Leu Cys Gly Pro Ile Thr Gly Phe Val Val Gln
 65                  70                  75                  80

Pro Cys Val Gly Val Trp Ser Asp Lys Cys Arg Ser Lys Tyr Gly Arg
                 85                  90                  95

Arg Arg Pro Phe Ile Leu Ala Gly Cys Val Leu Ile Cys Ala Ala Val
                100                 105                 110

Thr Leu Val Gly Phe Ser Ala Asp Leu Gly Tyr Met Leu Gly Asp Thr
            115                 120                 125
```

-continued

```
Thr Glu His Cys Ser Thr Tyr Lys Gly Leu Arg Tyr Arg Ala Ala Phe
        130                 135                 140

Ile Phe Ile Phe Gly Phe Trp Met Leu Asp Leu Ala Asn Asn Thr Val
145                 150                 155                 160

Gln Gly Pro Ala Arg Ala Leu Leu Ala Asp Leu Ser Gly Pro Asp Gln
                165                 170                 175

Cys Asn Ser Ala Asn Ala Ile Phe Cys Ser Trp Met Ala Val Gly Asn
                180                 185                 190

Val Leu Gly Phe Ser Ala Gly Ala Ser Gly Asn Trp His Lys Trp Phe
            195                 200                 205

Pro Phe Leu Met Thr Arg Ala Cys Cys Glu Ala Cys Gly Asn Leu Lys
    210                 215                 220

Ala Ala Phe Leu Ile Ala Val Val Phe Leu Leu Phe Cys Met Ala Val
225                 230                 235                 240

Thr Leu Tyr Phe Ala Glu Glu Ile Pro Leu Glu Pro Lys Asp Ala Gln
                245                 250                 255

Gln Leu Ser Asp Ser Ala Pro Leu Leu Asn Gly Ser Arg Asp Asp His
                260                 265                 270

Asp Ala Ser Ser Glu Gln Thr Asn Gly Gly Leu Ser Asn Gly His Ala
            275                 280                 285

Asp Ala Asn His Val Ser Ala Asn Ser Ser Ala Asp Ala Gly Ser Asn
    290                 295                 300

Ser Asn Lys Asp Asp Val Glu Ala Phe Asn Asp Gly Pro Gly Ala Val
305                 310                 315                 320

Leu Val Lys Ile Leu Thr Ser Met Arg His Leu Pro Pro Gly Met Tyr
                325                 330                 335

Ser Val Leu Leu Val Met Ala Leu Thr Trp Leu Ser Trp Phe Pro Phe
            340                 345                 350

Phe Leu Phe Asp Thr Asp Trp Met Gly Arg Glu Val Tyr His Gly Asp
    355                 360                 365

Pro Lys Gly Asn Ala Ser Glu Arg Lys Ala Tyr Asp Asp Gly Val Arg
370                 375                 380

Glu Gly Ala Phe Gly Leu Leu Leu Asn Ser Val Val Leu Gly Ile Gly
385                 390                 395                 400

Ser Phe Leu Ile Asp Pro Leu Cys Arg Met Ile Gly Ala Arg Leu Val
                405                 410                 415

Trp Ala Ile Ser Asn Phe Ile Val Phe Ala Cys Met Leu Ala Thr Thr
                420                 425                 430

Ile Leu Ser Trp Ile Ser Tyr Asp Leu Tyr Ser Ser Lys Leu Gln His
            435                 440                 445

Ile Val Gly Ala Asp Lys Thr Val Lys Thr Ser Ala Leu Ile Leu Phe
    450                 455                 460

Ser Leu Leu Gly Leu Pro Leu Ser Ile Thr Tyr Ser Val Pro Phe Ser
465                 470                 475                 480

Val Thr Ala Glu Leu Thr Ala Gly Thr Gly Gly Gln Gly Leu Ala
                485                 490                 495

Thr Gly Val Leu Asn Leu Ala Ile Val Ala Pro Gln Ile Val Val Ser
            500                 505                 510

Leu Gly Ala Gly Pro Trp Asp Lys Leu Leu Gly Gly Asn Val Pro
    515                 520                 525

Ala Phe Ala Leu Ala Ser Val Phe Ser Leu Ala Ala Gly Val Leu Ala
530                 535                 540
```

-continued

```
Val Ile Lys Leu Pro Lys Leu Ser Asn Asn Tyr Gln Ser Ala Gly Phe
545                 550                 555                 560

His Met Gly

<210> SEQ ID NO 25
<211> LENGTH: 501
<212> TYPE: PRT
<213> ORGANISM: Daucus carota

<400> SEQUENCE: 25

Met Ala Gly Pro Glu Ala Asp Arg Asn Arg His Arg Gly Gly Ala Thr
1               5                   10                  15

Ala Ala Pro Pro Arg Ser Arg Val Ser Leu Arg Leu Leu Leu Arg
                20                  25                  30

Val Ala Ser Val Ala Cys Gly Ile Gln Phe Gly Trp Ala Leu Gln Leu
        35                  40                  45

Ser Leu Leu Thr Pro Tyr Val Gln Glu Leu Gly Ile Pro His Ala Trp
    50                  55                  60

Ser Ser Ile Ile Trp Leu Cys Gly Pro Leu Ser Gly Leu Leu Val Gln
65                  70                  75                  80

Pro Ile Val Gly His Met Ser Asp Gln Cys Thr Ser Lys Tyr Gly Arg
                85                  90                  95

Arg Arg Pro Phe Ile Val Ala Gly Gly Thr Ala Ile Ile Leu Ala Val
                100                 105                 110

Ile Ile Ile Ala His Ser Ala Asp Ile Gly Gly Leu Leu Gly Asp Thr
            115                 120                 125

Ala Asp Asn Lys Thr Met Ala Ile Val Ala Phe Val Ile Gly Phe Trp
            130                 135                 140

Ile Leu Asp Val Ala Asn Asn Met Thr Gln Gly Pro Cys Arg Ala Leu
145                 150                 155                 160

Leu Ala Asp Leu Thr Gly Asn Asp Ala Arg Arg Thr Arg Val Ala Asn
                165                 170                 175

Ala Tyr Phe Ser Leu Phe Met Ala Ile Gly Asn Val Leu Gly Tyr Ala
                180                 185                 190

Thr Gly Ala Tyr Ser Gly Trp Tyr Lys Val Phe Pro Phe Ser Leu Thr
            195                 200                 205

Ser Ser Cys Thr Ile Asn Cys Ala Asn Leu Lys Ser Ala Phe Tyr Ile
    210                 215                 220

Asp Ile Ile Phe Ile Ile Thr Thr Tyr Ile Ser Ile Ser Ala Ala
225                 230                 235                 240

Lys Glu Arg Pro Arg Ile Ser Ser Gln Asp Gly Pro Gln Phe Ser Glu
                245                 250                 255

Asp Gly Thr Ala Gln Ser Gly His Ile Glu Glu Ala Phe Leu Trp Glu
            260                 265                 270

Leu Phe Gly Thr Phe Arg Leu Leu Pro Gly Ser Val Trp Val Ile Leu
        275                 280                 285

Leu Val Thr Cys Leu Asn Trp Ile Gly Trp Phe Pro Phe Ile Leu Phe
    290                 295                 300

Asp Thr Asp Trp Met Gly Arg Glu Ile Tyr Gly Gly Glu Pro Asn Gln
305                 310                 315                 320

Gly Gln Ser Tyr Ser Asp Gly Val Arg Met Gly Ala Phe Gly Leu Met
                325                 330                 335

Met Asn Ser Val Val Leu Gly Ile Thr Ser Val Leu Met Glu Lys Leu
            340                 345                 350
```

```
Cys Arg Ile Trp Gly Ser Gly Phe Met Trp Gly Leu Ser Asn Ile Leu
            355                 360                 365

Met Thr Ile Cys Phe Phe Ala Met Leu Leu Ile Thr Phe Ile Ala Lys
    370                 375                 380

Asn Met Asp Tyr Gly Thr Asn Pro Pro Asn Gly Ile Val Ile Ser
385                 390                 395                 400

Ala Leu Ile Val Phe Ala Ile Leu Gly Ile Pro Leu Ala Ile Thr Tyr
                405                 410                 415

Ser Val Pro Tyr Ala Leu Val Ser Thr Arg Ile Glu Ser Leu Gly Leu
            420                 425                 430

Gly Gln Gly Leu Ser Met Gly Val Leu Asn Leu Ala Ile Val Val Pro
            435                 440                 445

Gln Val Ile Val Ser Leu Gly Ser Gly Pro Trp Asp Gln Leu Phe Gly
    450                 455                 460

Gly Gly Asn Ser Pro Ala Phe Val Val Ala Ala Leu Ser Ala Phe Ala
465                 470                 475                 480

Ala Gly Leu Ile Ala Leu Ile Ala Ile Arg Arg Pro Arg Val Asp Lys
                485                 490                 495

Ser Arg Leu His His
            500

<210> SEQ ID NO 26
<211> LENGTH: 537
<212> TYPE: PRT
<213> ORGANISM: Oryza sativa

<400> SEQUENCE: 26

Met Ala Arg Gly Ser Gly Ala Gly Gly Gly Gly Gly Gly Gly Gly Gly
1               5                   10                  15

Gly Leu Glu Leu Ser Val Gly Val Gly Gly Gly Ala Arg Gly Gly
            20                  25                  30

Gly Gly Gly Glu Ala Ala Ala Ala Val Glu Thr Ala Ala Pro Ile Ser
        35                  40                  45

Leu Gly Arg Leu Ile Leu Ser Gly Met Val Ala Gly Gly Val Gln Tyr
    50                  55                  60

Gly Trp Ala Leu Gln Leu Ser Leu Leu Thr Pro Tyr Val Gln Thr Leu
65                  70                  75                  80

Gly Leu Ser His Ala Leu Thr Ser Phe Met Trp Leu Cys Gly Pro Ile
                85                  90                  95

Ala Gly Met Val Val Gln Pro Cys Val Gly Leu Tyr Ser Asp Arg Cys
                100                 105                 110

Thr Ser Lys Trp Gly Arg Arg Pro Tyr Ile Leu Thr Gly Cys Val
            115                 120                 125

Leu Ile Cys Leu Ala Val Val Val Ile Gly Phe Ser Ala Asp Ile Gly
    130                 135                 140

Tyr Ala Met Gly Asp Thr Lys Glu Asp Cys Ser Val Tyr His Gly Ser
145                 150                 155                 160

Arg Trp His Ala Ala Ile Val Tyr Val Leu Gly Phe Trp Leu Leu Asp
                165                 170                 175

Phe Ser Asn Asn Thr Val Gln Gly Pro Ala Arg Ala Leu Met Ala Asp
            180                 185                 190

Leu Ser Gly Arg His Gly Pro Gly Thr Ala Asn Ser Ile Phe Cys Ser
            195                 200                 205

Trp Met Ala Met Gly Asn Ile Leu Gly Tyr Ser Ser Gly Ser Thr Asn
    210                 215                 220
```

-continued

```
Asn Trp His Lys Trp Phe Pro Phe Leu Lys Thr Arg Ala Cys Cys Glu
225                 230                 235                 240

Ala Cys Ala Asn Leu Lys Gly Ala Phe Leu Val Ala Val Ile Phe Leu
                245                 250                 255

Ser Leu Cys Leu Val Ile Thr Leu Ile Phe Ala Lys Glu Val Pro Phe
            260                 265                 270

Lys Gly Asn Ala Ala Leu Pro Thr Lys Ser Asn Glu Pro Ala Glu Pro
        275                 280                 285

Glu Gly Thr Gly Pro Leu Ala Val Leu Lys Gly Phe Arg Asn Leu Pro
    290                 295                 300

Thr Gly Met Pro Ser Val Leu Ile Val Thr Gly Leu Thr Trp Leu Ser
305                 310                 315                 320

Trp Phe Pro Phe Ile Leu Tyr Asp Thr Asp Trp Met Gly Arg Glu Ile
                325                 330                 335

Tyr His Gly Asp Pro Lys Gly Thr Asp Pro Gln Ile Glu Ala Phe Asn
            340                 345                 350

Gln Gly Val Arg Ala Gly Ala Phe Gly Leu Leu Leu Asn Ser Ile Val
        355                 360                 365

Leu Gly Phe Ser Ser Phe Leu Ile Glu Pro Met Cys Arg Lys Val Gly
    370                 375                 380

Pro Arg Val Val Trp Val Thr Ser Asn Phe Leu Val Cys Ile Ala Met
385                 390                 395                 400

Ala Ala Thr Ala Leu Ile Ser Phe Trp Ser Leu Lys Asp Phe His Gly
                405                 410                 415

Thr Val Gln Lys Ala Ile Thr Ala Asp Lys Ser Ile Lys Ala Val Cys
            420                 425                 430

Leu Val Leu Phe Ala Phe Leu Gly Val Pro Leu Ala Val Leu Tyr Ser
        435                 440                 445

Val Pro Phe Ala Val Thr Ala Gln Leu Ala Ala Thr Arg Gly Gly Gly
    450                 455                 460

Gln Gly Leu Cys Thr Gly Val Leu Asn Ile Ser Ile Val Ile Pro Gln
465                 470                 475                 480

Val Val Ile Ala Leu Gly Ala Gly Pro Trp Asp Glu Leu Phe Gly Lys
                485                 490                 495

Gly Asn Ile Pro Ala Phe Gly Leu Ala Ser Gly Phe Ala Leu Ile Gly
            500                 505                 510

Gly Val Ala Gly Ile Phe Leu Leu Pro Lys Ile Ser Lys Arg Gln Phe
        515                 520                 525

Trp Ser Val Ser Met Gly Gly Gly His
    530                 535

<210> SEQ ID NO 27
<211> LENGTH: 533
<212> TYPE: PRT
<213> ORGANISM: Ricinus communis

<400> SEQUENCE: 27

Met Gln Ser Ser Thr Ser Lys Glu Asn Lys Gln Pro Pro Ser Ser Gln
  1               5                  10                  15

Pro His Pro Pro Pro Leu Met Val Ala Gly Ala Ala Glu Pro Asn Ser
            20                  25                  30

Ser Pro Leu Arg Lys Val Val Met Val Ala Ser Ile Ala Ala Gly Ile
        35                  40                  45

Gln Phe Gly Trp Ala Leu Gln Leu Ser Leu Leu Thr Pro Tyr Val Gln
```

```
            50                  55                  60
Leu Leu Gly Ile Pro His Thr Trp Ala Ala Phe Ile Trp Leu Cys Gly
 65                  70                  75                  80

Pro Ile Ser Gly Met Leu Val Gln Pro Ile Val Gly Tyr His Ser Asp
                 85                  90                  95

Arg Cys Thr Ser Arg Phe Gly Arg Arg Pro Phe Ile Ala Ser Gly
                100                 105                 110

Ala Ala Phe Val Ala Ile Ala Val Phe Leu Ile Gly Tyr Ala Ala Asp
                115                 120                 125

Leu Gly His Leu Ser Gly Asp Ser Leu Asp Lys Ser Pro Lys Thr Arg
130                 135                 140

Ala Ile Ala Ile Phe Val Val Gly Phe Trp Ile Leu Asp Val Ala Asn
145                 150                 155                 160

Asn Met Leu Gln Gly Pro Cys Arg Ala Leu Leu Ala Asp Leu Ser Gly
                165                 170                 175

Thr Ser Gln Lys Lys Thr Arg Thr Ala Asn Ala Leu Phe Ser Phe Phe
                180                 185                 190

Met Ala Val Gly Asn Val Leu Gly Tyr Ala Ala Gly Ala Tyr Thr His
                195                 200                 205

Leu Tyr Lys Leu Phe Pro Phe Thr Lys Thr Thr Ala Cys Asp Val Tyr
210                 215                 220

Cys Ala Asn Leu Lys Ser Cys Phe Phe Ile Ser Ile Val Leu Leu Leu
225                 230                 235                 240

Ser Leu Thr Val Leu Ala Leu Ser Tyr Val Lys Glu Lys Pro Trp Ser
                245                 250                 255

Pro Asp Gln Ala Val Asp Asn Ala Glu Asp Asp Thr Ala Ser Gln Ala
                260                 265                 270

Ser Ser Ser Ala Gln Pro Met Pro Phe Phe Gly Glu Ile Leu Gly Ala
                275                 280                 285

Phe Lys Asn Leu Lys Arg Pro Met Trp Ile Leu Leu Leu Val Thr Cys
                290                 295                 300

Leu Asn Trp Ile Ala Trp Phe Pro Phe Leu Leu Phe Asp Thr Asp Trp
305                 310                 315                 320

Met Gly Arg Glu Val Tyr Gly Gly Asp Ser Ser Gly Ser Ala Glu Gln
                325                 330                 335

Leu Lys Leu Tyr Asp Arg Gly Val Arg Ala Gly Ala Leu Gly Leu Met
                340                 345                 350

Leu Asn Ser Val Val Leu Gly Phe Thr Ser Leu Gly Val Glu Val Leu
                355                 360                 365

Ala Arg Gly Val Gly Gly Val Lys Arg Leu Trp Gly Ile Val Asn Phe
                370                 375                 380

Val Leu Ala Val Cys Leu Ala Met Thr Val Leu Val Thr Lys Gln Ala
385                 390                 395                 400

Glu Ser Thr Arg Arg Phe Ala Thr Val Ser Gly Gly Ala Lys Val Pro
                405                 410                 415

Leu Pro Pro Pro Ser Gly Val Lys Ala Gly Ala Leu Ala Leu Phe Ala
                420                 425                 430

Val Met Gly Val Pro Gln Ala Ile Thr Tyr Ser Ile Pro Phe Ala Leu
                435                 440                 445

Ala Ser Ile Phe Ser Asn Thr Ser Gly Ala Gly Gln Gly Leu Ser Leu
                450                 455                 460

Gly Val Leu Asn Leu Ser Ile Val Ile Pro Gln Met Ile Val Ser Val
465                 470                 475                 480
```

```
Ala Ala Gly Pro Trp Asp Ala Leu Phe Gly Gly Gly Asn Leu Pro Ala
            485                 490                 495

Phe Val Val Gly Ala Val Ala Leu Ala Ser Gly Ile Phe Ala Leu
            500                 505                 510

Thr Met Leu Pro Ser Pro Gln Pro Asp Met Pro Ser Ala Lys Ala Leu
            515                 520                 525

Thr Ala Ala Phe His
            530

<210> SEQ ID NO 28
<211> LENGTH: 523
<212> TYPE: PRT
<213> ORGANISM: Vicia faba

<400> SEQUENCE: 28

Met Glu Pro Leu Ser Ser Thr Lys Gln Ile Asn Asn Asn Asn Asn Leu
 1               5                  10                  15

Ala Lys Pro Ser Ser Leu His Val Glu Thr Gln Pro Leu Glu Pro Ser
                20                  25                  30

Pro Leu Arg Lys Ile Met Val Val Ala Ser Ile Ala Ala Gly Val Gln
            35                  40                  45

Phe Gly Trp Ala Leu Gln Leu Ser Leu Leu Thr Pro Tyr Val Gln Leu
        50                  55                  60

Leu Gly Ile His His Thr Trp Ala Ala Tyr Ile Trp Leu Cys Gly Pro
 65                 70                  75                  80

Ile Ser Gly Met Leu Val Gln Pro Ile Val Gly Tyr His Ser Asp Arg
                85                  90                  95

Cys Thr Ser Arg Phe Gly Arg Arg Pro Phe Ile Ala Ala Gly Ser
            100                 105                 110

Ile Ala Val Ala Ile Ala Val Phe Leu Ile Gly Tyr Ala Ala Asp Leu
            115                 120                 125

Gly His Ser Phe Gly Asp Ser Leu Asp Gln Lys Val Arg Pro Arg Ala
        130                 135                 140

Ile Gly Ile Phe Val Val Gly Phe Trp Ile Leu Asp Val Ala Asn Asn
145                 150                 155                 160

Met Leu Gln Gly Pro Cys Arg Ala Leu Leu Gly Asp Leu Cys Ala Gly
                165                 170                 175

Asn Gln Arg Lys Thr Arg Asn Ala Asn Ala Phe Phe Ser Phe Phe Met
            180                 185                 190

Ala Val Gly Asn Val Leu Gly Tyr Ala Ala Gly Ala Tyr Ser Lys Leu
        195                 200                 205

Tyr His Val Phe Pro Phe Thr Lys Thr Lys Ala Cys Asn Val Tyr Cys
    210                 215                 220

Ala Asn Leu Lys Ser Cys Phe Phe Leu Ser Ile Ala Leu Leu Thr Val
225                 230                 235                 240

Leu Ala Thr Ser Ala Leu Ile Tyr Val Lys Glu Thr Ala Leu Thr Pro
                245                 250                 255

Glu Lys Thr Val Val Thr Thr Glu Asp Gly Gly Ser Ser Gly Gly Met
            260                 265                 270

Pro Cys Phe Gly Gln Leu Ser Gly Ala Phe Lys Glu Leu Lys Arg Pro
        275                 280                 285

Met Trp Ile Leu Leu Leu Val Thr Cys Leu Asn Trp Ile Ala Trp Phe
    290                 295                 300

Pro Phe Leu Leu Phe Asp Thr Asp Trp Met Gly Lys Glu Val Tyr Gly
```

-continued

```
305                 310                 315                 320
Gly Thr Val Gly Glu Gly His Ala Tyr Asp Met Gly Val Arg Glu Gly
                325                 330                 335
Ala Leu Gly Leu Met Leu Asn Ser Val Val Leu Gly Ala Thr Ser Leu
                340                 345                 350
Gly Val Asp Ile Leu Ala Arg Gly Val Gly Gly Val Lys Arg Leu Trp
                355                 360                 365
Gly Ile Val Asn Phe Leu Leu Ala Ile Cys Leu Gly Leu Thr Val Leu
        370                 375                 380
Val Thr Lys Leu Ala Gln His Ser Arg Gln Tyr Ala Pro Gly Thr Gly
385                 390                 395                 400
Ala Leu Gly Asp Pro Leu Pro Pro Ser Glu Gly Ile Lys Ala Gly Ala
                405                 410                 415
Leu Thr Leu Phe Ser Val Leu Gly Val Pro Leu Ala Ile Thr Tyr Ser
                420                 425                 430
Ile Pro Phe Ala Leu Ala Ser Ile Phe Ser Ser Thr Ser Gly Ala Gly
                435                 440                 445
Gln Gly Leu Ser Leu Gly Val Leu Asn Leu Ala Ile Val Ile Pro Gln
        450                 455                 460
Met Phe Val Ser Val Leu Ser Gly Pro Trp Asp Ala Leu Phe Gly Gly
465                 470                 475                 480
Gly Asn Leu Pro Ala Phe Val Val Gly Ala Val Ala Ala Leu Ala Ser
                485                 490                 495
Gly Ile Leu Ser Ile Ile Leu Leu Pro Ser Pro Pro Asp Met Ala
                500                 505                 510
Lys Ser Val Ser Ala Thr Gly Gly Gly Phe His
        515                 520
```